US007697967B2

(12) United States Patent
Stafford

(10) Patent No.: US 7,697,967 B2
(45) Date of Patent: Apr. 13, 2010

(54) METHOD AND APPARATUS FOR PROVIDING ANALYTE SENSOR INSERTION

(75) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 422 days.

(21) Appl. No.: 11/535,983

(22) Filed: Sep. 28, 2006

(65) Prior Publication Data
US 2008/0033268 A1    Feb. 7, 2008

Related U.S. Application Data

(60) Provisional application No. 60/754,870, filed on Dec. 28, 2005.

(51) Int. Cl.
*A61B 5/00*    (2006.01)
(52) U.S. Cl. .................. 600/345; 600/347; 600/365; 600/584
(58) Field of Classification Search .......... 600/345, 600/547, 365, 576, 583; 606/182, 185, 181
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |

(Continued)

FOREIGN PATENT DOCUMENTS

EP    0098592    1/1984

(Continued)

OTHER PUBLICATIONS

International Search Report and Written Opinion of the International Searching Authority for PCT Application No. PCT/US2007/079774 filed Sep. 27, 2007 to Abbott Diabetes Care, Inc.

(Continued)

*Primary Examiner*—Robert L Nasser
(74) *Attorney, Agent, or Firm*—Jackson & Co., LLP

(57) ABSTRACT

Devices and methods for positioning a portion of a sensor at a first predetermined location, displacing the portion of the sensor from the first predetermined location to a second predetermined location, and detecting one or signals associated with an analyte level of a patient at the second predetermined location are disclosed. Also provided are systems and kits for use in analyte monitoring.

20 Claims, 17 Drawing Sheets

U.S. PATENT DOCUMENTS

| | | | |
|---|---|---|---|
| 4,671,288 A | 6/1987 | Gough | |
| 4,703,756 A | 11/1987 | Gough et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,854,322 A | 8/1989 | Ash et al. | |
| 4,890,620 A | 1/1990 | Gough | |
| 4,895,147 A * | 1/1990 | Bodicky et al. | 606/182 |
| 4,925,268 A | 5/1990 | Iyer et al. | |
| 4,953,552 A | 9/1990 | DeMarzo | |
| 4,986,271 A | 1/1991 | Wilkins | |
| 4,988,341 A | 1/1991 | Columbus et al. | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,082,550 A | 1/1992 | Rishpon et al. | |
| 5,106,365 A | 4/1992 | Hernandez | |
| 5,122,925 A | 6/1992 | Inpyn | |
| 5,165,407 A | 11/1992 | Wilson et al. | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,584,813 A | 12/1996 | Livingston et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,735,285 A | 4/1998 | Albert et al. | |
| 5,772,586 A | 6/1998 | Heinonen et al. | |
| 5,791,344 A | 8/1998 | Schulman et al. | |
| 5,807,375 A | 9/1998 | Gross et al. | |
| 5,851,197 A | 12/1998 | Marano et al. | |
| 5,899,855 A | 5/1999 | Brown | |
| 5,925,021 A | 7/1999 | Castellano et al. | |
| 5,942,979 A | 8/1999 | Luppino | |
| 5,957,854 A | 9/1999 | Besson et al. | |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,024,699 A | 2/2000 | Surwit et al. | |
| 6,049,727 A | 4/2000 | Crothall | |
| 6,083,710 A | 7/2000 | Heller et al. | |
| 6,088,608 A | 7/2000 | Schulman et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,159,147 A | 12/2000 | Lichter et al. | |
| 6,162,611 A | 12/2000 | Heller et al. | |
| 6,175,752 B1 | 1/2001 | Say et al. | |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,275,717 B1 | 8/2001 | Gross et al. | |
| 6,283,761 B1 | 9/2001 | Joao | |
| 6,283,982 B1 | 9/2001 | Levaughn et al. | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,348,640 B1 | 2/2002 | Navot et al. | |
| 6,359,444 B1 | 3/2002 | Grimes | |
| 6,360,888 B1 | 3/2002 | McIvor et al. | |
| 6,366,794 B1 | 4/2002 | Moussy et al. | |
| 6,377,828 B1 | 4/2002 | Chaiken et al. | |
| 6,379,301 B1 | 4/2002 | Worthington et al. | |
| 6,424,847 B1 | 7/2002 | Mastrototaro et al. | |
| 6,427,088 B1 | 7/2002 | Bowman, IV et al. | |
| 6,440,068 B1 | 8/2002 | Brown et al. | |
| 6,478,736 B1 | 11/2002 | Mault | |
| 6,484,046 B1 | 11/2002 | Say et al. | |
| 6,514,718 B2 | 2/2003 | Heller et al. | |
| 6,522,927 B1 | 2/2003 | Bishay et al. | |
| 6,551,494 B1 | 4/2003 | Heller et al. | |
| 6,558,320 B1 | 5/2003 | Causey, III et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,591,125 B1 | 7/2003 | Buse et al. | |
| 6,595,919 B2 | 7/2003 | Berner et al. | |
| 6,605,200 B1 | 8/2003 | Mao et al. | |
| 6,605,201 B1 | 8/2003 | Mao et al. | |
| 6,607,509 B2 | 8/2003 | Bobroff et al. | |

| Patent Number | Date | Inventor(s) |
|---|---|---|
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,276,029 B2 | 10/2007 | Goode, Jr. et al. |
| 7,278,983 B2 | 10/2007 | Ireland, et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,340,309 B2 * | 3/2008 | Miazga et al. ............... 607/115 |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister, et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 2002/0019022 A1 | 2/2002 | Dunn et al. |
| 2002/0022855 A1 | 2/2002 | Bobroff et al. |
| 2002/0042090 A1 | 4/2002 | Heller et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0161288 A1 | 10/2002 | Shin et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0134347 A1 | 7/2003 | Heller et al. |
| 2003/0144581 A1 | 7/2003 | Conn et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0106858 A1 | 6/2004 | Say et al. |
| 2004/0106859 A1 | 6/2004 | Say et al. |
| 2004/0122353 A1 | 6/2004 | Shahmirian et al. |
| 2004/0133164 A1 * | 7/2004 | Funderburk et al. ......... 604/134 |
| 2004/0135684 A1 | 7/2004 | Steinthal et al. |
| 2004/0138588 A1 | 7/2004 | Saikley et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0090607 A1 | 4/2005 | Tapsak et al. |
| 2005/0112169 A1 | 5/2005 | Brauker et al. |
| 2005/0114068 A1 | 5/2005 | Chey et al. |
| 2005/0121322 A1 | 6/2005 | Say et al. |

| | | |
|---|---|---|
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0222518 A1 | 10/2005 | Dib |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1* | 1/2006 | Brister et al. ............... 600/345 |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2007/0016381 A1 | 1/2007 | Kamath et al. |
| 2007/0027381 A1 | 2/2007 | Stafford |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0114280 A1 | 5/2008 | Stafford |
| 2008/0119707 A1 | 5/2008 | Stafford |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |

| | | |
|---|---|---|
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/05089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/120363 | 10/2007 |
| WO | WO-2008/031106 | 3/2008 |
| WO | WO-2008/031110 | 3/2008 |
| WO | WO-2008/051920 | 5/2008 |
| WO | WO-2008/051924 | 5/2008 |
| WO | WO-2008/103620 | 8/2008 |
| WO | WO-2008/150917 | 12/2008 |

OTHER PUBLICATIONS

Armour, J. C., et al., "Application of Chronic Intravascular Blood Glucose Sensor in Dogs", *Diabetes*, vol. 39, 1990, pp. 1519-1526.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Mediated Enzyme Electrode for Amperometric Determination of Glucose", *Analytical Chemistry*, vol. 56, No. 4, 1984, 667-671.
Complaint, "*Abbott Diabetes Care, Inc. v. Dexcom, Inc.*", filed Aug. 11, 2005.
Complaint, Amended, "*Abbott Diabetes Care, Inc. v. Dexcom, Inc.*", filed Jun. 27, 2006.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain The Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp.937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Preliminary Report on Patentability and Written Opinion of the International Searching Authority for PCT Application No. PCT/US2007/079774 filed Sep. 27, 2007 mailed Apr. 9, 2009.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp. 1061-1071.

Schmidt, F. J., et al., "Calibration of a Wearable Glucose Sensor", *The International Journal of Artificial Organs*, vol. 15, No. 1, 1992, pp. 55-61.

U.S. Patent Reexamination No. 90/008,172, Request for Reexamination of U.S. Patent No. 6,990,366 filed Aug. 16, 2006.

U.S. Patent Reexamination No. 90/008,457, Request for Reexamination of U.S. Patent No. 6,990,366 filed Jan. 23, 2007.

U.S. Patent Reexamination No. 90/009,104, Request for Reexamination of U.S. Patent No. 6,990,366 filed Apr. 8, 2008.

U.S. Patent Reexamination No. 90/009,328, Request for Reexamination of U.S. Patent No. 6,990,366 filed Nov. 10, 2008.

U.S. Patent Reexamination No. 90/010,791, Request for Reexamination of U.S. Patent No. 6,990,366 filed Dec. 22, 2009.

* cited by examiner

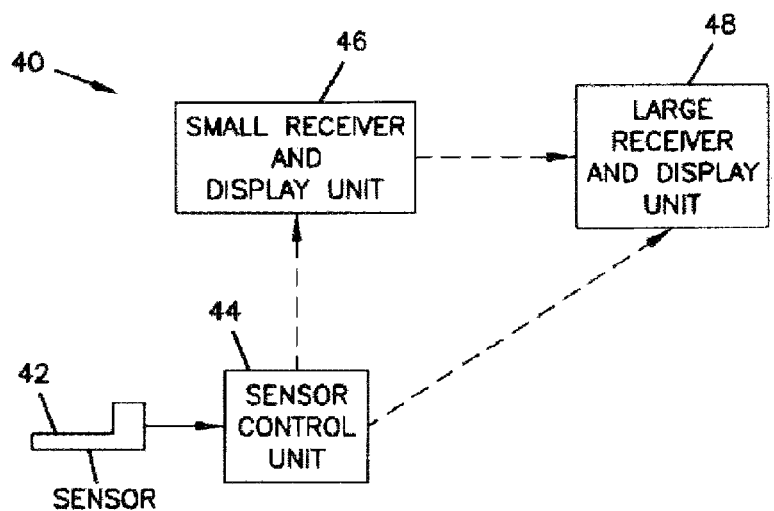
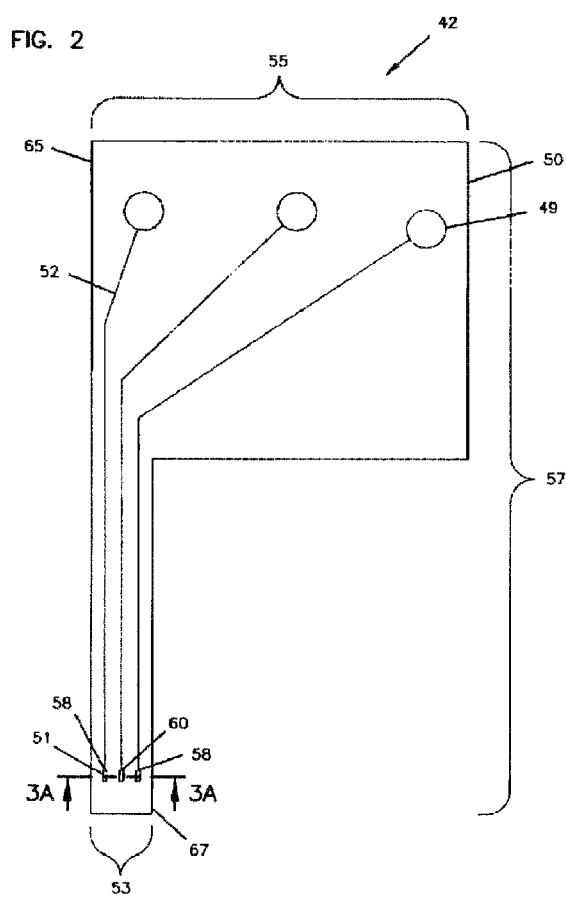
FIGURE 1

FIG. 3A
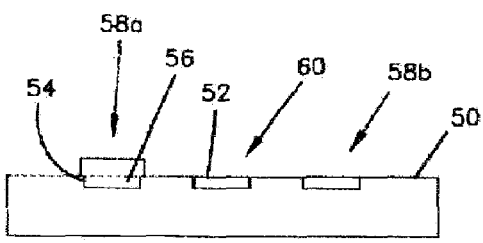
FIG. 3B
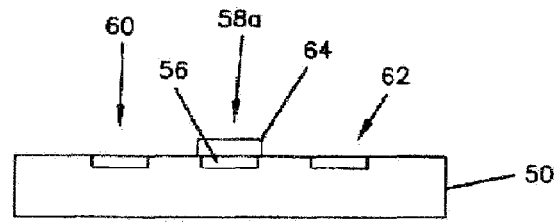
FIG. 4A
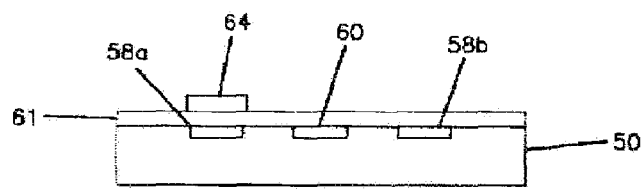
FIG. 4B
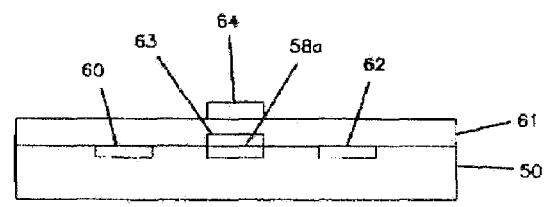
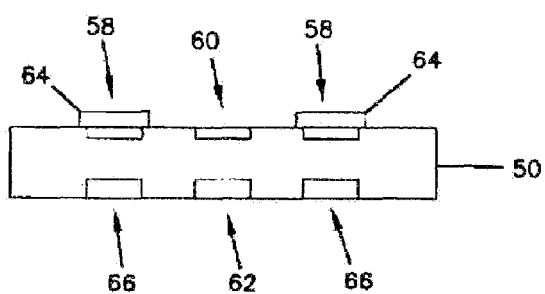
FIGURE 5

METHOD AND APPARATUS FOR PROVIDING ANALYTE SENSOR INSERTION

RELATED APPLICATION

The present application claims priority to provisional application No. 60/754,870 filed on Dec. 28, 2005 entitled "Medical Device Insertion", the disclosure of which is incorporated in its entirety by reference for all purposes.

BACKGROUND OF THE INVENTION

There are many instances in which it is necessary to position at least a portion of a medical device beneath the epidermis of a patient, e.g., in the subcutaneous layer or elsewhere.

For example, the monitoring of the level of glucose or other analytes, such as lactate or oxygen or the like, in certain individuals is vitally important to their health. The monitoring of glucose is particularly important to individuals with diabetes, as they must determine when insulin is needed to reduce glucose levels in their bodies or when additional glucose is needed to raise the level of glucose in their bodies.

In this regard, devices have been developed for continuous or automatic monitoring of analytes, such as glucose, in the blood stream or interstitial fluid. Many of these analyte measuring devices are configured so that at least a portion of the devices is positioned below the epidermis, e.g., in a blood vessel or in the subcutaneous tissue of a patient.

These devices, as well as other medical devices, may be positioned manually, e.g., by a user or a healthcare worker, or automatically or semi-automatically with the aid of a sensor positioning device. Regardless of the manner in which the device is inserted beneath the skin, it is important that the device positioning process does not adversely affect the operation of the device. Furthermore, it is important that pain is minimal.

As interest in inserting medical devices, e.g., continuous analyte monitoring devices, beneath the epidermis of a patient continues, there is interest in devices and methods for operably inserting such devices. Of interest are such devices and methods that have minimal impact on device function and which produce minimal pain. Of particular interest are continuous analyte monitoring positioning devices that enable clinically accurate analyte information to be obtained substantially immediately following device positioning in a patient.

SUMMARY OF THE INVENTION

Generally, the present invention relates to methods and devices for positioning a medical device at least partially beneath the epidermal layer of skin. In certain embodiments, the present invention relates to the continuous and/or automatic in vivo monitoring of the level of an analyte using an analyte sensor and more specifically devices and methods for operably positioning analyte sensors at least partially beneath the epidermal layer of skin. The subject invention is further described with respect to positioning an analyte sensing device (also referred to herein as a "sensor", "analyte monitoring device/sensor", and the like) and analyte sensing systems, where such description is in no way intended to limit the scope of the invention. It is understood that the subject invention is applicable to any medical device in which at least a portion of the device is intended to be positioned beneath the epidermis.

Embodiments of the subject invention include analyte sensor positioning devices and methods that are adapted to provide clinically accurate analyte data (e.g., analyte-related signal) substantially immediately after a sensor has been operably positioned in a patient (e.g., at least a portion of the sensor in the subcutaneous tissue, or elsewhere).

Embodiments of the subject invention include systems in which the period of time after a sensor is positioned in a patient, when a first (or only) sensor calibration is required, is substantially reduced (excluding any factory-set calibration) and/or the number of calibrations (excluding any factory-set calibration) is reduced, e.g., to three or less calibrations, e.g., two or less calibrations, e.g., one calibration or no calibrations.

Also provided are sensor positioning devices and methods that at least minimize, and in many instances eliminate, the occurrence of periods of spurious, low analyte readings, e.g., substantially immediately following sensor positioning, during the night, etc.

Embodiments include devices and methods that modulate the sensor positioning speed, or stated otherwise the rate at which a sensor is delivered to a site in a patient, e.g., using at least two different velocities.

Also provided are positioning devices and methods that operably position a sensor in a site of a patient using an acute angle, relative to the skin.

Embodiments also include sensor positioning devices and methods that employ an anesthetic agent.

Aspects include minimal pain, including substantially pain-free, sensor positioning methods and devices and sensor positioning methods and devices that do not substantially interfere with sensor function.

Also provided are systems and kits.

BRIEF DESCRIPTION OF THE DRAWINGS

The invention may be more completely understood in consideration of the following detailed description of various embodiments of the invention in connection with the accompanying drawings, in which:

FIG. 1 shows a block diagram of an exemplary embodiment of an analyte monitor using an implantable analyte sensor, according to the invention;

FIG. 2 is a top view of one embodiment of an analyte sensor, according to the invention;

FIG. 3A is a cross-sectional view of the analyte sensor of FIG. 2;

FIG. 3B is a cross-sectional view of another embodiment of an analyte sensor, according to the invention;

FIG. 4A is a cross-sectional view of another embodiment of an analyte sensor, according to the invention;

FIG. 4B is a cross-sectional view of a fourth embodiment of another embodiment of a sensor, according to the invention;

FIG. 5 is a cross-sectional view of another embodiment of an analyte sensor, according to the invention;

DEFINITIONS

Figure 6:
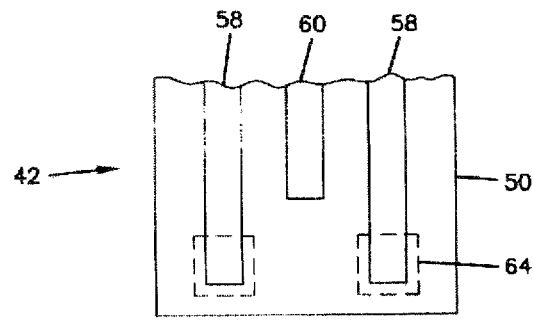
FIG. 6 is an expanded top view of a tip-portion of the analyte sensor of FIG. 2.

Throughout the present application, unless a contrary intention appears, the following terms refer to the indicated characteristics.

A "biological fluid" or "physiological fluid" or "body fluid", is any body fluid in which an analyte can be measured, for example, blood, interstitial fluid, dermal fluid, sweat, tears, and urine. "Blood" includes whole blood and its cell-free components, such as, plasma and serum.

A "counter electrode" refers to an electrode paired with the working electrode, through which passes a current equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is entrapped on or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes mobility. For example, in certain embodiments an anesthetic agent or precursor thereof may be immobilized within a sensor.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte (or a second compound whose level depends on the level of the analyte) is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and conductive polymers.

When one item is indicated as being "remote" from another, this is referenced that the two items are at least in different buildings, and may be at least one mile, ten miles, or at least one hundred miles apart. When different items are indicated as being "local" to each other they are not remote from one another (for example, they can be in the same building or the same room of a building). "Communicating", "transmitting" and the like, of information reference conveying data representing information as electrical or optical signals over a suitable communication channel (for example, a private or public network, wired, optical fiber, wireless radio or satellite, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item. When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that it is apparent that one is related to the other such as where one references the other.

Items of data are "linked" to one another in a memory when a same data input (for example, filename or directory name or search term) retrieves those items (in a same file or not) or an input of one or more of the linked items retrieves one or more of the others.

It will also be appreciated that throughout the present application, that words such as "cover", "base" "front", "back", "top", "upper", and "lower" are used in a relative sense only.

"May" refers to optionally.

When two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the present invention is related to analyte sensor positioning devices and methods (the term "positioning" is used herein interchangeably with "delivery", "insertion", and the like). The present invention is applicable to an analyte monitoring system using a sensor—at least a portion of which is positionable beneath the skin of the user for the in vivo determination of a concentration of an analyte, such as glucose, lactate, and the like, in a body fluid. The sensor may be, for example, subcutaneously positionable in a patient for the continuous or periodic monitoring an analyte in a patient's interstitial fluid. This may be used to infer the glucose level in the patient's bloodstream. The sensors of the subject invention also include in vivo analyte sensors insertable into a vein, artery, or other portion of the body containing fluid. A sensor of the subject invention is typically configured for monitoring the level of the analyte over a time period which may range from minutes, hours, days, weeks, or longer. Of interest are analyte sensors, such as glucose sensors, that are capable of providing analyte data for about one hour or more, e.g., about a few hours or more, e.g., about a few days of more, e.g., about three or more days, e.g., about five days or more, e.g., about seven days or more, e.g., about several weeks or months.

Embodiments include positioning devices and systems, and methods that provide clinically accurate analyte data (e.g., relative to a reference) substantially immediately, as shown by any suitable technique known to those of skill in the art, e.g., a Clark Error Grid, Parks Error Grid, Continuous Glucose Error Grid, MARD analysis, and the like. For example, in those embodiments in which the sensor is a continuous sensor and at least a portion of the sensor is adapted to be positioned under the skin of a patient, the sensor is adapted to provide clinically accurate analyte data (e.g., relative to a reference) substantially immediately after the sensor is operably positioned in a patient. In other words, the waiting period from the time a sensor is positioned in a user and the time clinically accurate data may be obtained and used by the user, is greatly reduced relative to prior art devices that require a greater waiting period before accurate analyte data may be obtained and used by a user. By "substantially immediately" is meant from about 0 hours to less than about 5 hours, e.g., from about 0 hours to about 3 hours, e.g., from about 0 hours to less than about 1 hour, e.g., from about 30 minutes or less, where in many embodiments the sensors according to the subject invention are capable of providing clinically accurate analyte data once the sensor has been operatively positioned in the patient.

As noted above, embodiments also include analyte monitoring devices and methods having substantially reduced (including eliminated) periods of time of spurious, low analyte readings, as compared to a control, i.e., the period of time in which clinically accurate analyte data is obtainable is greater, as compared to a control. The subject invention may be employed to minimize or eliminate spurious low analyte readings obtained at any time during sensor use, including a period of time immediately after sensor activation (e.g., positioning of an analyte sensor in or on a patient) and/or anytime thereafter. Accordingly, embodiments include sensors positioning devices and methods that enable sensors to provide clinically accurate analyte data substantially immediately after the sensor has been operably positioned in a patient (e.g., in the subcutaneous tissue, etc.) and/or without substantial interruption due to spurious analyte readings Embodiments include minimal tissue trauma-producing analyte positioning devices and methods, where embodiments include modulating the rate at which a sensor is delivered to a target site. For example, at least two velocities may be used in the positioning of a sensor, where embodiments include a multiple rate sensor delivery protocol having a first sensor delivery rate, followed by a second sensor delivery rate that is less than the first. Embodiments may include opening the skin with a first velocity, and inserting the sensor through the thus-formed skin opening to a target site (e.g., into the subcutaneous tissue) with a second, minimal tissue trauma-producing velocity, where the second velocity is less than the first velocity. Such may be accomplished automatically or semi-automatically with a sensor positioning device. The positioning device may include a sharp portion and a sensor-carrying portion and may be adapted to provide a skin incision and position a sensor in a patient using variable speeds. It is to be understood that such may be accomplished wholly or at least partially manually.

Certain embodiments include two-stage sensor delivery devices and methods and include devices capable of producing at least first and second velocities. Specific embodiments include devices capable of producing a superficial cut in the skin that is no deeper than the epidermis using a first velocity, and inserting the sensor through the thus-formed cut to a target site using a second velocity that is slower than the first velocity. The speed of the first velocity may be selected to minimize the patient's perception of pain and the speed of the second velocity may be selected to minimize tissue damage at the site of eventual glucose measurements. For example, the high speed of the first velocity (e.g., from about 4 to about 8 m/s in certain embodiments) may minimize the patient's pain while the slower speed of the second velocity (e.g., from about 0.025 to about 0.5 m/s in certain embodiments) may minimize the damage due to the tissue at the site of the eventual glucose sensor measurements. Accordingly, a user contacts the device to a skin surface and actuates the device to cut the skin and insert the sensor through the cut to the target site, using at least two different velocities for the incision forming and sensor delivery operations.

The various velocities employed may differ by any suitable amount. For example, in certain embodiments in which two velocities are employed, the velocities may differ by about 25% to about 95%, e.g., by about 60% to about 90%. Velocity change may be gradual or stepped. The change in velocity may be perceptible to the user or not, where in many embodiments the velocity change is not perceptible by the user. In certain embodiments, the sensor positioning process is automatic in that a user need only activate the device, e.g., actuate a button, lever, contact with a skin surface, or the like, to initiate the sensor positioning process, which process then proceeds to completion without any further user intervention. However, in some embodiments one or more parameters may be controllable by the user, e.g., the timing of velocity change, magnitudes of velocity(ies), etc.

Embodiments of the above-described two-speed sensor insertion minimize tissue damage to the superficial layer of the skin, the stratum corneum and epidermis, as a greater force is required to penetrate these outer layers of the skin, and hence a greater likelihood of tissue damage. By limiting the depth of the incision to the upper layers of the skin, i.e., the stratum corneum and epidermis, minimization of tissue damage at the site of the eventual analyte sensor placement in the subcutaneous adipose tissue layer is achieved.

Furthermore, since in certain embodiments a separate sharp is not employed to penetrate below the outer layer of skin, not only is the tissue damage in the subcutaneous adipose layer minimized by use of the slower speed in the second velocity portion of the insertion, but the physical size and dimension of the wound is greatly reduced by eliminating the use of a separate sharp device penetrating below the outer layer of the skin.

In certain embodiments, the sharp device which disrupts the stratum corneum and epidermis may penetrate from about 0.5 mm to about 1.5 mm below the surface of the skin in certain embodiments. In certain analyte sensing systems, the analyte-sensing chemistry layer on the sensor, by contrast, may be positioned below or deeper than this penetration, e.g., below about 0.5 mm to about 1.5 mm below the surface of the skin. The slow speed of the second velocity portion of the insertion displaces the adipose cells in the subcutaneous adipose tissue layer rather than physically disrupting the cells and effectively coring out a cylinder in which the sensor may be subsequently placed. By contrast, in the present invention, the slow speed of the second velocity portion of the insertion minimizes the volume of tissue which has been removed or even displaced by the sensor insertion. As a result, the sensing portion of the sensor is in immediate proximal contact with the surrounding tissue. In contrast to typical insertion methods in which a cylindrical core of tissue is displaced or removed by a high-speed insertion, in the present invention there is no open volume of tissue in which fluids may accumulate forming edema typical of wound response to trauma of this nature. The absence of or the significant reduction of edema in the present invention associated with the minimization of the perturbed volume of tissue contributes to rapid sensor equilibration with the method of sensor insertion described herein compared with conventional sensor insertion procedures.

Embodiments include making a large wide cut through the epidermis, then a much smaller incision in terms of its cross-sectional dimensions through the dermis and into the underlying subcutaneous adipose tissue layer, where in certain embodiments as much as about a fourfold difference in the cross-sectional area (e.g., 0.48 mm$^2$ for the incision in the epidermis compared to 0.12 mm$^2$ for the incision in the subcutaneous layer).

The subject invention also includes anesthetic agents in sensor positioning. That is, certain embodiments include sensor positioning devices, methods and/or sensors that include an anesthetic agent ("active agent"). The active agent may be any suitable anesthetic agent(s) known or to be discovered. Examples of anesthetic agents include, but are not limited to, lidocaine (with or without epinephrine), prilocaine, bupivacaine, benzocaine, and ropivacaine, marcaine (with or without epinephrine) and the like, and combinations thereof, and well as cold sprays such as ethyl chloride sprays.

The active-agent containing devices may be analyte sensors and/or analyte sensor positioning devices in certain embodiments, and/or may be a structure that is positionable near a skin location site at which site an incision is or will be made and sensor is or will be inserted (a body fluid sampling site). In certain embodiments, the structure may be a sensor positioning device, drug delivery device (e.g., insulin delivery device), etc.

In certain embodiments, active agent may not be carried by a device, but rather may be otherwise applied at or substantially near the sensor insertion site. Accordingly, embodiments include systems having an active agent delivery unit and an analyte sensor.

Active agent employed in the subject invention may be delivered transdermally, by a topical route, formulated as applicator sticks, solutions, suspensions, emulsions, gels, creams, ointments, pastes, jellies, paints, powders, and aerosols. For example, embodiments may include an active agent in the form of a discrete patch or film or plaster or the like adapted to remain in intimate contact with the epidermis of the recipient for a period of time. For example, such transdermal patches may include a base or matrix layer, e.g., polymeric layer, in which active agent is retained. The base or matrix layer may be operably associated with a support or backing. Active agents suitable for transdermal administration may also be delivered by iontophoresis and may take the form of an optionally buffered aqueous solution that includes the active agent. Suitable formulations may include citrate or bis/tris buffer (pH 6) or ethanol/water and contain a suitable amount of active ingredient.

Active agents may be applied via parenteral administration, such as intravenous ("IV") administration, intramuscular ("IM"), subcutaneous ("SC" or "SQ"), mucosal. The formulations for such administration may include a solution of the active agent dissolved in a pharmaceutically acceptable carrier. Among the acceptable vehicles and solvents that may be employed, include, but are not limited to, water and Ringer's solution, an isotonic sodium chloride, etc. Active agent may be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter.

In other embodiments, the active agent may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). Methods for preparing liposomal suspensions are known in the art and thus will not be described herein in great detail.

Embodiments may also include administration of active agent using an active agent administration device other than a sensor positioning device and a sensor such as, but not limited to, pumps (implantable or external devices and combinations of both (e.g., certain components may be implantable and others may be external to the body such as controls for the implantable components), epidural injectors, syringes or other injection apparatus, catheter and/or reservoir operably associated with a catheter, etc. For example, in certain embodiments a device employed to deliver active agent to a subject may be a pump, syringe, catheter or reservoir operably associated with a connecting device such as a catheter, tubing, or the like. Containers suitable for delivery of active agent to an active agent administration device include instruments of containment that may be used to deliver, place, attach, and/or insert the active agent into the delivery device for administration of the active agent to a subject and include, but are not limited to, vials, ampules, tubes, capsules, bottles, syringes and bags. Embodiments may also include administration of active agent via a biodegradable implant active agent delivery device. Such may be accomplished by employing syringes to deposit such a biodegradable delivery device under the skin of a subject. The implants degrade completely, so that removal is not necessary.

Embodiments may include employing an electrode to deliver active agent to a subject. For example, an electrode may be used that has a small port at its tip which is connected to a reservoir or pump containing active agent. The active agent delivery electrode may be implanted using any suitable technique such as surgical cut down, laparoscopy, endoscopy, percutaneous procedure, and the like. In certain embodiments a reservoir or pump may also be implanted in the subject's body. The active agent delivery electrode, or other analogous device, may be controllable such that the amount of active agent delivered, the rate at which the active agent may be delivered, and the time period over which the active agent may be delivered, etc., may be controllable and may be adjusted, e.g., by a user and/or healthcare worker.

Accordingly, embodiments include contacting an analyte determination site with active agent, and determining the concentration of an analyte, where the contacting may be by way of an analyte sensor, analyte sensor positioning device or other structure, transdermal administration, parenteral administration, etc.

In those embodiments in which a sensor positioning device and/or sensor or other device includes active agent, the active agent-containing structure may include or incorporate active agent in any suitable manner. For example, at least a portion of a positioning device and/or sensor, e.g., a body fluid-contacting portion, may include active agent, where in certain embodiments substantially the entire positioning device and/or sensor may include active agent. Active agent may be immobilized on a surface of a positioning device and/or sensor or may be configured to diffuse away from a surface of a positioning device and/or sensor. In certain embodiments, at least the portion of the positioning device that is adapted to provide a skin incision, e.g., a sharp of a sensor positioning device, may include active agent.

In certain embodiments, active agent is a coating on at least a portion of positioning device and/or sensor. In certain embodiments, active agent is incorporated, e.g., embedded, or otherwise integrated into a positioning device and/or sensor.

A positioning device and/or sensor may also have the ability to emit or diffuse active agent at a controllable rate, e.g., may include a controlled release, such as a time release, formulation. For example, a positioning device and/or sensor may include a formulation that is designed to release active agent gradually over time, e.g., over about a period of time commensurate with sensor positioning. A controlled release formulation may employ a polymer or other non-anesthetic agent material to control the release of the active agent. The active agent release rate may be slowed by diffusion through the polymer, or the active agent may be released as the polymer degrades or disintegrates in the body.

The active agent may be added to a positioning device and/or sensor during fabrication thereof and/or may be applied after fabrication. For example, a coating containing active agent thereof may be applied to a positioning device and/or sensor after it has been fabricated.

Active agent may be applied to a positioning device and/or sensor by any of a variety of methods, e.g., by spraying the active agent onto at least a portion of a positioning device and/or sensor or by dipping a positioning device and/or sensor into the active agent, or otherwise immersing or flooding a positioning device and/or sensor with the active agent.

The amount of active agent employed may vary depending on a variety of factors such as the particular active agent used, the particulars of the positioning device and/or sensor, etc. In any event, an effective amount of active agent is used—an amount sufficient to provide the requisite anesthetic result for the desired period of time.

Representative analyte sensors, analyte monitoring systems and sensor positioning devices are now described, where such description is for exemplary purposes only and is in no way intended to limit the scope of the invention.

Analyte Sensors and Sensor Systems

The analyte sensors and analyte monitoring systems of the present invention can be utilized under a variety of conditions. The particular configuration of a sensor and other units used in an analyte monitoring system may depend on the use for which the sensor and system are intended and the conditions under which the sensor and system will operate. As noted above, embodiments include a sensor configured for implantation into a patient or user. The term "implantation" is meant broadly to include wholly implantable sensors and sensors in which only a portion of which is implantable under the skin and a portion of which resides above the skin, e.g., for contact to a transmitter, receiver, transceiver, processor, etc. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be desired, in some cases, to limit the depth of implantation of the sensor. Sensors may also be implanted in other regions of the body to determine analyte levels in other fluids. Examples of suitable sensors for use in the analyte monitoring systems of the invention are described in U.S. Pat. Nos. 6,134,461, 6,175,752, and elsewhere.

An exemplary embodiment of an analyte monitoring system 40 for use with an implantable sensor 42, e.g., for use with a subcutaneously implantable sensor, is illustrated in block diagram form in FIG. 1. The analyte monitoring system 40 includes, at minimum, a sensor 42, at least a portion of the sensor which is configured for implantation (e.g., subcutaneous, venous, or arterial implantation) into a patient, and a sensor control unit 44. The sensor 42 is coupleable to the sensor control unit 44 which is typically attachable to the skin of a patient. The sensor control unit 44 operates the sensor 42, including, for example, providing a voltage across the electrodes of the sensor 42 and collecting signals from the sensor 42.

The sensor control unit 44 may evaluate the signals from the sensor 42 and/or transmit the signals to one or more optional receiver/display units 46, 48 for evaluation. The sensor control unit 44 and/or the receiver/display units 46, 48 may display or otherwise communicate the current level of the analyte. Furthermore, the sensor control unit 44 and/or the receiver/display units 46, 48 may indicate to the patient, via, for example, an audible, visual, or other sensory-stimulating alarm, when the level of the analyte is at or near a threshold level. In some embodiments, an electrical shock may be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

A sensor 42 includes at least one working electrode 58 and a substrate 50, as shown in FIG. 2. The sensor 42 may also include at least one counter electrode 60 (or counter/reference electrode) and/or at least one reference electrode 62 (see for example FIG. 7). The counter electrode 60 and/or reference electrode 62 may be formed on the substrate 50 or may be separate units. For example, the counter electrode and/or reference electrode may be formed on a second substrate which is also implantable in the patient or, for some embodiments of the sensors the counter electrode and/or reference electrode may be placed on the skin of the patient with the working electrode or electrodes being implanted into the patient. The use of an on-the-skin counter and/or reference electrode with an implantable working electrode is described in, e.g., U.S. Pat. No. 5,593,852.

The working electrode or electrodes 58 are formed using conductive materials 52. The counter electrode 60 and/or reference electrode 62, as well as other optional portions of the sensor 42, such as a temperature probe 66 (see for example FIG. 7), may also be formed using conductive material 52. The conductive material 52 may be formed over a smooth surface of the substrate 50 or within channels 54 formed by, for example, embossing, indenting or otherwise creating a depression in the substrate 50.

A sensing layer 64 (see for example FIGS. 3, 4, 5 and 6) may be provided proximate to or on at least one of the working electrodes 58 to facilitate the electrochemical detection of the analyte and the determination of its level in the sample fluid, particularly if the analyte can not be electrolyzed at a desired rate and/or with a desired specificity on a bare electrode.

In addition to the electrodes 58, 60, 62 and the sensing layer 64, the sensor 42 may also include optional components such as one or more of the following: a temperature probe 66 (see for example FIGS. 5 and 7), a mass transport limiting layer 74, e.g., a matrix such as a membrane or the like, (see for example FIG. 8), a biocompatible layer 75 (see for example FIG. 8), and/or other optional components, as described below. Each of these optional items enhances the functioning of and/or results from the sensor 42, as discussed below.

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In addition to considerations regarding flexibility, it is often desirable that a sensor 42 should have a substrate 50 which is non-toxic. Preferably, the substrate 50 is approved by one or more appropriate governmental agencies or private groups for in vivo use. Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2.

At least one conductive trace 52 may be formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces may extend close to the tip of the sensor 42 to minimize the amount of the sensor that must be implanted.

The conductive traces may be formed using a conductive material 56 such as carbon (e.g., graphite), a conductive polymer, a metal or alloy (e.g., gold or gold alloy), or a metallic compound (e.g., ruthenium dioxide or titanium dioxide), or the like. Conductive traces 52 (and channels 54, if used) may be formed with relatively narrow widths. In embodiments with two or more conductive traces 52 on the same side of the substrate 50, the conductive traces 52 are separated by distances sufficient to prevent conduction between the conductive traces 52. The working electrode 58 and the counter electrode 60 (if a separate reference electrode is used) may be made using a conductive material 56, such as carbon.

The reference electrode 62 and/or counter/reference electrode may be formed using conductive material 56 that is a suitable reference material, for example silver/silver chloride or a non-leachable redox couple bound to a conductive material, for example, a carbon-bound redox couple.

The electrical contact 49 may be made using the same material as the conductive material 56 of the conductive traces 52, or alternatively, may be made from a carbon or other non-metallic material, such as a conducting polymer.

A number of exemplary electrode configurations are described below, however, it will be understood that other configurations may also be used. In certain embodiments, e.g., illustrated in FIG. 3A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown for example in FIG. 3B. Each of these embodiments is illustrated with all of the electrodes formed on the same side of the substrate 50.

Figure 7:
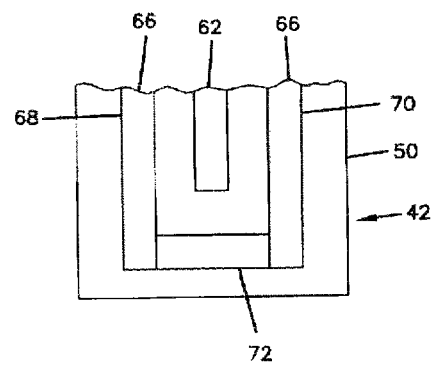
FIG. 7 is an expanded bottom view of a tip-portion of the analyte sensor of FIG. 2.

Alternatively, one or more of the electrodes may be formed on an opposing side of the substrate 50. In another embodiment, two working electrodes 58 and one counter electrode 60 are formed on one side of the substrate 50 and one reference electrode 62 and a temperature probe 66 are formed on an opposing side of the substrate 50, as illustrated in FIG. 6. The opposing sides of the tip of this embodiment of the sensor 42 are illustrated in FIGS. 6 and 7.

Some analytes, such as oxygen, may be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode 58. For these analytes, each working electrode 58 has a sensing layer 64 formed proximate to or on a working surface of the working electrode 58. In many embodiments, the sensing layer 64 is formed near or on only a small portion of the working electrode 58, e.g., near a tip of the sensor 42.

The sensing layer 64 includes one or more components designed to facilitate the electrolysis of the analyte. The sensing layer 64 may be formed as a solid composition of the desired components (e.g., an electron transfer agent and/or a catalyst). These components may be non-leachable from the sensor 42 and may be immobilized on the sensor 42. For example, the components may be immobilized on a working electrode 58. Alternatively, the components of the sensing layer 64 may be immobilized within or between one or more membranes or films disposed over the working electrode 58 or the components may be immobilized in a polymeric or sol-gel matrix. Examples of immobilized sensing layers are described in, e.g., U.S. Pat. Nos. 5,262,035; 5,264,104; 5,264, 105; 5,320,725; 5,593,852; and 5,665,222; and PCT Patent Application No. US98/02403 entitled "Soybean Peroxidase Electrochemical Sensor".

Sensors having multiple working electrodes 58a may also be used, e.g., and the signals therefrom may be averaged or measurements generated at these working electrodes 58a may be averaged. In addition, multiple readings at a single working electrode 58a or at multiple working electrodes may be averaged.

In many embodiments, the sensing layer 64 contains one or more electron transfer agents in contact with the conductive material 56 of the working electrode 58, as shown for example in FIGS. 3 and 4 and 5. Useful electron transfer agents and methods for producing them are described in, e.g., U.S. Pat. Nos. 5,264,104; 5,356,786; 5,262,035; and 5,320,725, 6,175,752, 6,329,161, and elsewhere.

The sensing layer 64 may also include a catalyst which is capable of catalyzing a reaction of the analyte. The catalyst may also, in some embodiments, act as an electron transfer agent.

To electrolyze the analyte, a potential (versus a reference potential) is applied across the working and counter electrodes 58, 60. When a potential is applied between the working electrode 58 and the counter electrode 60, an electrical current will flow.

Those skilled in the art will recognize that there are many different reactions that will achieve the same result; namely the electrolysis of an analyte or a compound whose level depends on the level of the analyte.

A variety of optional items may be included in the sensor. One optional item is a temperature probe 66 (see for example FIG. 7). One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72. The temperature probe 66 can provide a temperature adjustment for the output from the working electrode 58 to offset the temperature dependence of the working electrode 58.

Figure 8:
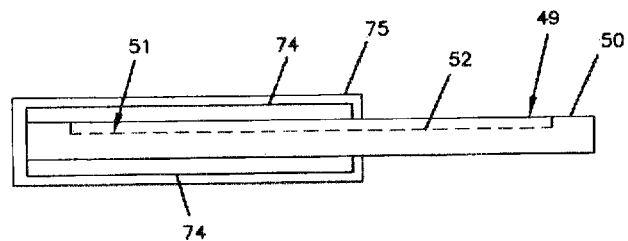
FIG. 8 is a side view of the analyte sensor of FIG. 2.

The sensors of the subject invention are biocompatible. Biocompatibility may be achieved in a number of different manners. For example, an optional biocompatible layer 74 may be formed over at least that portion of the sensor 42 which is inserted into the patient, as shown in FIG. 8.

An interferant-eliminating layer (not shown) may be included in the sensor 42. The interferant-eliminating layer may include ionic components, such as Nafion® or the like, incorporated into a polymeric matrix to reduce the permeability of the interferant-eliminating layer to ionic interferants having the same charge as the ionic components.

A mass transport limiting layer 74 may be included with the sensor to act as a diffusion-limiting barrier to reduce the rate of mass transport of the analyte, for example, glucose or lactate, into the region around the working electrodes 58. Exemplary layers that may be used are described for example, in U.S. Pat. No. 6,881,551, and elsewhere.

A sensor of the subject invention may be adapted to be a replaceable component in an in vivo analyte monitor, and particularly in an implantable analyte monitor. As described above, in many embodiments the sensor is capable of operation over a period of days or more, e.g., a period of operation may be at least about one day, e.g., at least about three days, e.g., at least about five days, e.g., at least about one week or more, e.g., one month or more. The sensor may then be removed and replaced with a new sensor.

As described above, sensor positioning devices are provided. Embodiments of the subject positioning devices include low impact, minimal pain-producing devices, where certain embodiments are configured to obtain clinically accurate analyte information substantially immediately after sensor positioning. Device embodiments include variable insertion speed devices. Embodiments of the two stage sensor inserters described herein include single use, disposable, self-contained Sensor Delivery Units ("SDU") which may be included in a continuous glucose monitoring system.

Figure 15:
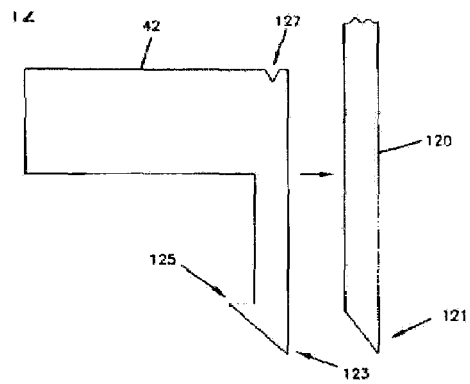
FIG. 15 is an expanded view of an exemplary embodiment of a sensor and a sensor positioning device, according to the invention.

Referring to FIG. 15, sensor positioning device 120 may be used to insert, e.g., subcutaneously insert, at least a portion of the sensor 42 into the patient. The sensor positioning device 120 may be formed using structurally rigid materials, such as metal or rigid plastic. Exemplary materials include, but are not limited to, stainless steel and ABS (acrylonitrile-butadiene-styrene) plastic. In some embodiments, the sensor positioning device 120 is pointed and/or sharp at the tip 121 to facilitate penetration of the skin of the patient. A sharp, thin sensor positioning device may reduce pain felt by the patient upon insertion of the sensor 42. In other embodiments, the tip 121 of the sensor positioning device 120 has other shapes, including a blunt or flat shape. These embodiments may be particularly useful when the sensor positioning device 120 does not penetrate the skin but rather serves as a structural support for the sensor 42 as the sensor 42 is pushed into the skin. In embodiments in which at least a portion of the positioning device includes an anesthetic agent, such may be included in any suitable location of device 120, e.g., at least a portion of tip 121.

Figure 16A:
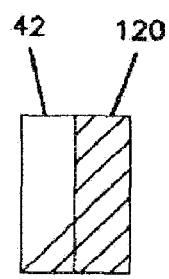
FIGS. 16A, 16B, 16C are cross-sectional views of three embodiments of the insertion device of FIG. 15.
Figure 16B:
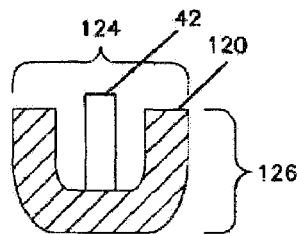
Figure 16C:
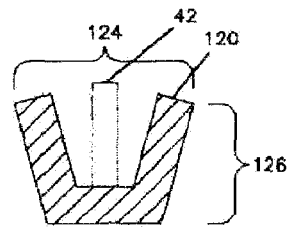

The sensor positioning device 120 may have a variety of cross-sectional shapes, as shown in FIGS. 16A, 16B, and 16C. The sensor positioning device 120 illustrated in FIG. 16A is a flat, planar, pointed strip of rigid material which may be attached or otherwise coupled to the sensor 42 to ease insertion of the sensor 42 into the skin of the patient, as well as to provide structural support to the sensor 42 during insertion. The sensor positioning devices 120 of FIGS. 16B and 16C are U- or V-shaped implements that support the sensor 42 to limit the amount that the sensor 42 may bend or bow during insertion. The cross-sectional width 124 of the sensor positioning devices 120 illustrated in FIGS. 16B and 16C may be about 1 mm or less, e.g., about 700 µm or less, e.g., about 500 µm or less, e.g., about 300 µm or less. The cross-sectional height 126 of the sensor positioning device 120 illustrated in FIGS. 16B and 16C may be about 1 mm or less, e.g., about 700 µm or less, e.g., about 500 µm or less in certain embodiments.

The sensor 42 itself may include optional features to facilitate insertion. For example, the sensor 42 may be pointed at the tip 123 to ease insertion, as illustrated in FIG. 15. In addition, the sensor 42 may include a barb 125 which helps retain the sensor 42 in the subcutaneous tissue of the patient. The barb 125 may also assist in anchoring the sensor 42 at the target site, e.g., within the subcutaneous tissue, of the patient during operation of the sensor 42. However, the barb 125 is typically small enough that little damage is caused to the subcutaneous tissue when the sensor 42 is removed for replacement. The sensor 42 may also include a notch 127 that can be used in cooperation with a corresponding structure (not shown) in the sensor positioning device to apply pressure against the sensor 42 during insertion, but disengage as the sensor positioning device 120 is removed. One example of such a structure in the sensor positioning device is a rod (not shown) between two opposing sides of a sensor positioning device 120 and at an appropriate height of the sensor positioning device 120.

In operation, a sensor is carried by the positioning device to the target site. For example, the sensor 42 is placed within or next to the sensor positioning device 120 (e.g., may be partially or completely held within the sharp of the device, e.g., in a nested configuration or the like) and then a force is provided against the sensor positioning device 120 and/or sensor 42 to carry the sensor 42 into the skin of the patient. As described above, in certain embodiments various speeds may be used in a given insertion, e.g., a first speed followed by a second speed where the first speed is greater relative to the second speed.

In one embodiment, the force is applied to the sensor 42 to push the sensor into the skin, while the sensor positioning device 120 remains stationary and provides structural support to the sensor 42. Alternatively, the force is applied to the sensor positioning device 120 and optionally to the sensor 42 to push a portion of both the sensor 42 and the sensor positioning device 120 through the skin of the patient and into the subcutaneous tissue. In any event, the forces used may be the same or different, as noted herein. The sensor positioning device 120 is optionally pulled out of the skin and subcutaneous tissue with the sensor 42 remaining in the subcutaneous tissue due to frictional forces between the sensor 42 and the patient's tissue. If the sensor 42 includes the optional barb 125, then this structure may also facilitate the retention of the sensor 42 within the interstitial tissue as the barb catches in the tissue. The force applied to the sensor positioning device 120 and/or the sensor 42 may be applied manually or mechanically. The sensor 42 is reproducibly inserted through the skin of the patient.

Figure 17:
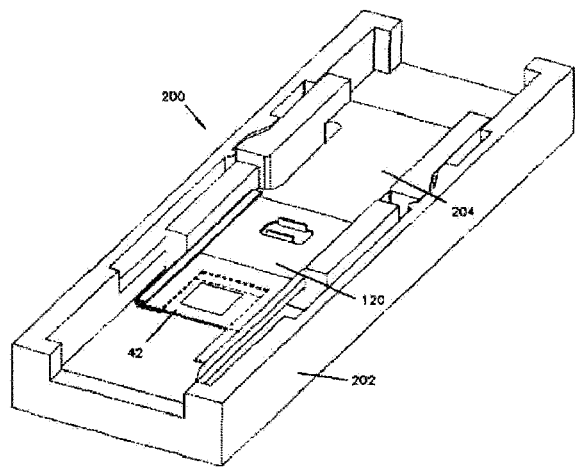
FIG. 17 is a perspective view of the internal structure of an exemplary embodiment of an insertion gun, according to the invention.

In certain embodiments, an insertion gun may be used to insert the sensor. One example of an insertion gun 200 for inserting a sensor 42 is shown in FIG. 17. The insertion gun 200 includes a housing 202 and a carrier 204. The sensor positioning device 120 is typically mounted on the carrier 204 and the sensor 42 is pre-loaded into the sensor positioning device 120. The carrier 204 drives the sensor 42 and, optionally, the sensor positioning device 120 into the skin of the patient using, for example, a cocked or wound spring, a burst of compressed gas, an electromagnet repelled by a second magnet, or the like, within the insertion gun 200. In some instances, for example, when using a spring, the carrier 204 and sensor positioning device may be moved, cocked, or otherwise prepared to be directed towards the skin of the patient.

After the sensor 42 is inserted, the insertion gun 200 may contain a mechanism which pulls the sensor positioning device 120 out of the skin of the patient. Such a mechanism may use a spring, electromagnet, or the like to remove the sensor positioning device 120.

The insertion gun may be reusable. The sensor positioning device 120 is often disposable to avoid the possibility of contamination. Alternatively, the sensor positioning device 120 may be sterilized and reused. In addition, the sensor positioning device 120 and/or the sensor 42 may be coated with an anticlotting agent to prevent fouling of the sensor 42.

In one embodiment, the sensor 42 is injected between about 2 to about 12 mm into the interstitial tissue of the patient for subcutaneous implantation, e.g., the sensor is injected about 3 to about 9 mm, e.g., about 5 to about 7 mm, into the interstitial tissue. Other embodiments of the invention may include sensors implanted in other portions of the patient, including, for example, in an artery, vein, or organ. The depth of implantation varies depending on the desired implantation target. In any event, in certain embodiments the injection is at a speed that differs from the speed employed to create an opening in the skin through which the sensor is injected.

Although the sensor 42 may be inserted anywhere in the body, it is often desirable that the insertion site be positioned so that the on-skin sensor control unit 44 may be concealed. In addition, it is often desirable that the insertion site be at a place on the body with a low density of nerve endings to reduce the pain to the patient. Examples of preferred sites for insertion of the sensor 42 and positioning of the on-skin sensor control unit 44 include the abdomen, thigh, leg, upper arm, and shoulder.

Any suitable angle of insertion may be used. An insertion angle is measured from the plane of the skin (i.e., inserting the sensor perpendicular to the skin would be a 90 degree insertion angle). As noted herein, in certain embodiments an angle less than about 90 degrees is used. The orientation of the two stage or two speed sensor inserter device may be either at normal angle to the skin or at an oblique angle to the skin such as but not limited to about 20, about 25, about 30, about 45 or about 60 degrees with respect to the skin surface itself. In contrast with the sensor used in the case of normal or 90 degree insertion, in instances in which other angles are used, the length of the sensor itself may be adjusted by standard trigonometric relations so that the actual depth of placement remains the same (e.g., remains comparable to that achieved using a 90 degree angle), e.g., in certain embodiments about 5.0 mm below the surface of the skin, i.e. in the midst of the subcutaneous adipose tissue layer.

The use of an angled insertion (i.e. less than about 90 degrees relative to the skin) in the present achieves physical separation of the superficial incision from the position in the tissue at which the sensor will be measuring the analyte of interest. Furthermore, the use of angled insertion may decrease the physical displacement of the sensor itself relative to the subcutaneous adipose tissue layer when physical pressure is applied to the sensor mount and transmitter in the course of a patient's normal daily living. This may be especially important for minimizing the occurrences of spurious low readings during periods of sleep.

The use of an angled insertion in the present invention takes advantage of the stratum corneum's reduced susceptibility to shear disruption or penetration compared with rupture due to direct normal insertion. Less force is required to penetrate the stratum corneum and the epidermis using an angled insertion than an insertion conducted at normal incidence. The latter may be accompanied by greater degrees of damage to the underlying tissue as well as the release of various chemical messengers active in the wound response of the epidermis and dermis.

Embodiments also include devices and methods for determining the thickness of the subcutaneous adipose tissue layer in a given individual at a given anatomical site such as the lower left or right abdominal quadrant or the posterior or lateral upper arm. Such devices and/or algorithms may be integrated with a positioning device or may be separate. For example, in the event that the subcutaneous adipose tissue layer at the desired location for the placement of the sensor is less than or approximately equal to a predetermined amount, e.g., about 5.0 mm, sensor lengths and/or angles which correctly place the active glucose transduction area of the sensor in the middle of the targeted subcutaneous adipose tissue layer may be determined and used.

Sensor positioning devices may involve manual, semi-automatic, or automatic operation, referring to the origin of the force that is used both to insert the sensor and to retract any portion of the sensor positioning device out of the skin of the patient that is not intended to remain inserted during the period of sensor operation. Semi-automatic or automatic operation refers to the incorporation of one or more forcegenerating methods, e.g., wound springs, compressed gas, electromagnet repulsion of a second magnet, and the like, either in combination with manual force or replacing manual force entirely, for the purpose of inserting the sensor and/or retracting any portion of the sensor positioning device out of the skin of the patient that is not intended to remain inserted during the period of sensor operation.

In certain embodiments, a plunger-type button is used as the actuation mechanism of an insertion gun. The button serves the purpose of releasing a compressed spring that drives the sharp tip of the sensor positioning device into the skin of the patient at a fast speed, consistent with minimizing pain, so as to create a superficial skin incision that is no deeper than the epidermis. The sharp tip of the positioning device may then be retracted out of the skin of the patient, manually or using a mechanism such as a spring, electromagnet, or the like. The continued travel of the actuator button would then also serve the purpose of manually driving the sensor into the skin, through the incision created by the sharp tip of the positioning device, at a velocity less than that used to create the incision.

In certain other embodiments of the device, the insertion gun includes a housing and a carrier. The sensor positioning device is typically mounted on the carrier and the sensor is pre-loaded into the sensor positioning device. The carrier drives the sensor positioning device into the skin of the patient using, for example, a cocked or wound spring, a burst of compressed gas, an electromagnet repelled by a second magnet, and the like, within the insertion gun. The velocity of the carrier may be decreased, after the creation of the superficial skin incision, through mechanical means e.g., viscous dashpots, air damping, friction, the addition of mass to the carrier, or the like. The continued motion of the carrier, for the purpose of inserting the sensor into the incision created by the sharp tip of the positioning device, would then occur at a velocity less than that used to create the incision. The sharp tip of the positioning device may be retracted out of the skin of the patient, either after the creation of the skin incision or after sensor insertion, manually or using a mechanism such as a spring, electromagnet, or the like.

Embodiments include a two stage or two velocity sensor inserter device that includes a base, housing, carrier/introducer/sensor assembly, high speed activation button, drive spring, return spring and manual plunger. These inserters may be provided to users fully assembled and armed with a sensor enclosed inside the introducer.

In use, the first stage of the insertion may begin by activating the device, e.g., by pressing the plunger and activation button, to cause the introducer to be propelled into the skin at a higher rate of speed than the speed that will be used at the second stage. The introducer makes a "shallow puncture", but does not release the sensor.

The "shallow puncture" depth may be controlled by the height and location of the latch ledge features on the housing, or the type and force (rate) of the drive spring or in other ways such as hard stop, increase of friction, magnets, safety lock, or dial (similar to a lancet device), and the like. The "shallow puncture" or superficial incision may not provide a channel into which the glucose sensor is placed, but rather may provide an opening in the upper layer of the skin only with mechanical strength.

After the "shallow puncture" or superficial incision is made through the stratum corneum and epidermis, the return spring retracts the sharp portion of the introducer out of the skin. The overall (uncompressed) height of the return spring positions the introducer/sensor slightly above the surface of the skin (puncture) for the second stage of the insertion.

When the first stage is activated (releasing the latches of the carrier mechanism), the high speed button comes to rest in a lower position on top of the housing, thereby leaving the plunger in the "up" and ready position. The introducer having made the puncture is now in the "next" position (with the sensor still intact).

The second stage of the insertion may be accomplished manually (e.g., similar to and approximately as slow or slower than injection via syringe) by the user. Pressing down on the plunger causes the introducer/carrier/sensor to move from the "next" position and continue into the shallow puncture until the prescribed sensor insertion depth is reached. The prescribed insertion depth may be controlled by the compressed (solid) height of the return spring or in some other way such as hard stop, adhesive mount, safety lock or other similar restraining or limiting device.

When the prescribed depth is reached, the sensor body may be captured by features on an adhesive mount mounted on the patient's skin and released from the introducer for contact with the transmitter which is connectable to the mount. The insertion is complete when the first phase has provided an opening through the outer layer of the skin and the second phase has resulted in the placement of the sensor at the desired depth in the subcutaneous adipose tissue layer, The user releases the plunger (e.g., by removing their finger) and the return spring causes the introducer to exit the skin and into the "safe for disposal position". The SDU may then be detached from the mount and discarded accordingly.

A sensor insertion such as described above may be accomplished with one hand and without the benefit of direct line of sight.

The two stage insertion process may be achieved in one motion, (e.g., by the user pressing the top of the plunger and pushing down until it comes to rest on the top of the housing). However, the user may make a "2 motion-2 stage" insertion (by pressing the plunger, stopping after the high speed button has been activated then pressing the plunger).

Figure 18A:
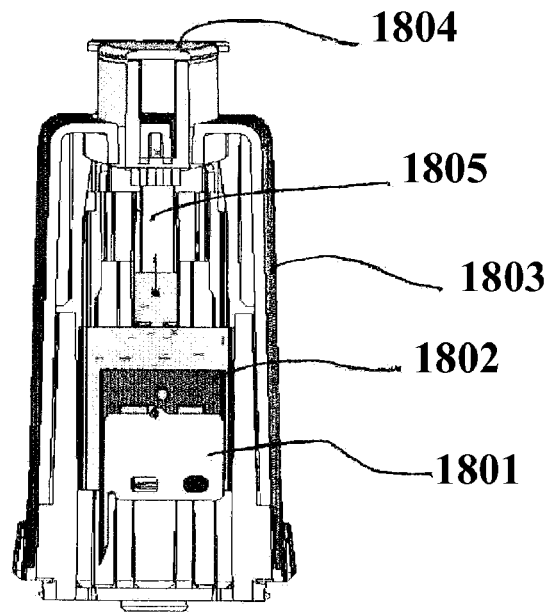
FIGS. 18A-18B are front component view and perspective view, respectively, of the two stage sensor insertion mechanism including the insertion device armed and ready for insertion, further illustrating the sensor introducer and sensor to make the first stage puncture, and also showing the plunger and the button in accordance with one embodiment of the present invention.
Figure 18B:
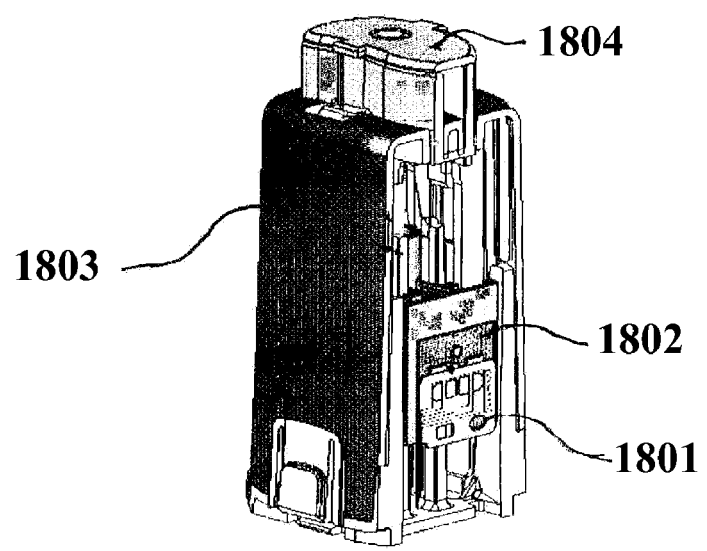

FIGS. 18A-18B are front component view and perspective view, respectively, of an exemplary embodiments of a two stage sensor insertion mechanism including the insertion device armed and ready for insertion, further illustrating the sensor introducer and sensor to make the first stage puncture, and also showing the plunger and the button in accordance with one embodiment of the present invention. Referring to the Figures, the insertion device in one embodiment includes sensor 1801 operatively coupled to a sensor introducer 1802 substantially provided in the housing 1803 of the sensor insertion mechanism. Also shown in the Figures is a trigger button 1804 operatively coupled to a plunger 1805 in one embodiment, and where the actuation of the trigger button 1804 may be configured to deploy the sensor 1801 to a first insertion depth under the skin layer of the patient, guided by the sensor introducer 1802.

Figure 19A:
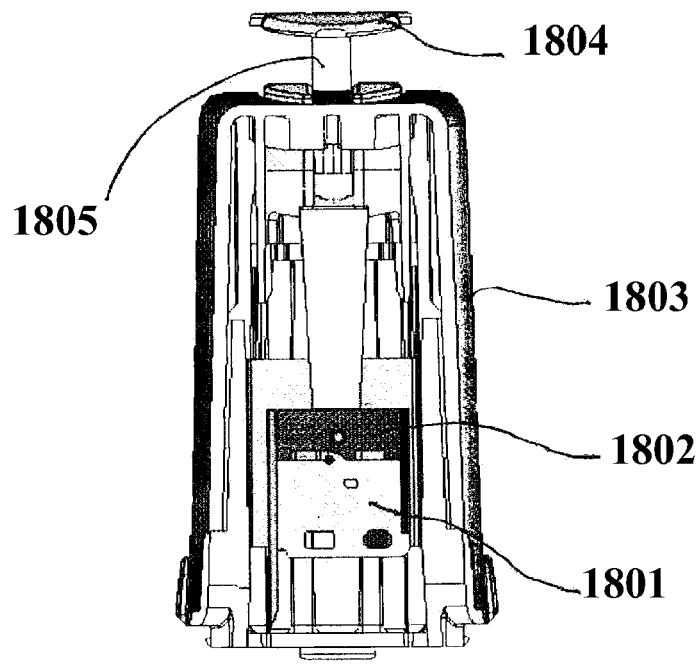
FIG. 19A illustrates a front component view of the two stage sensor insertion mechanism after the firing of the first stage trigger button to achieve the initial puncture, and with the plunger exposed for the second stage insertion activation, and also illustrating the sensor/introducer position after the initial first stage puncture (for example, at 1.55 mm depth) in accordance with one embodiment of the present invention.

FIG. 19A illustrates a front component view of the two stage sensor insertion mechanism after the firing of the first stage trigger button to achieve the initial puncture, and with the plunger exposed for the second stage insertion activation, and also illustrating the sensor/introducer position after the initial first stage puncture (for example, at 1.55 mm depth) in accordance with one embodiment of the present invention.

Figure 19B:
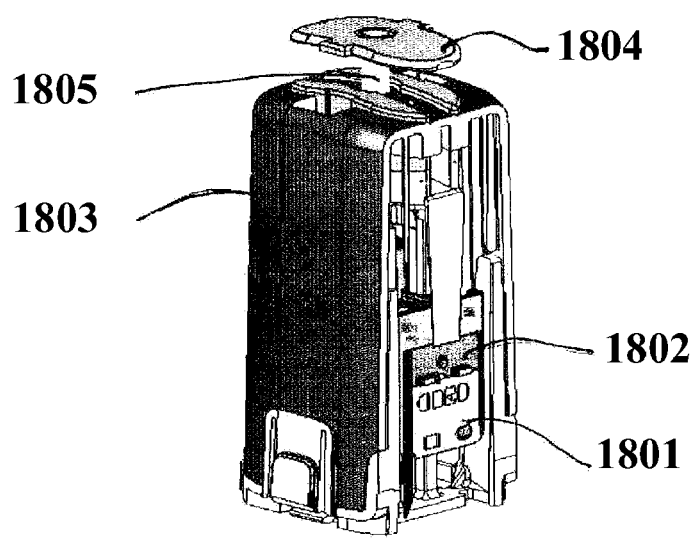
FIGS. 19B-19D illustrate a perspective view, a close-up perspective view, and a side view, respectively, of the two stage sensor insertion mechanism after the first stage trigger button firing shown in FIG. 19A, where the side view shown in FIG. 19D further illustrates the special relationship of the carrier and drive spring with the plunger and the trigger button.
Figure 19C:
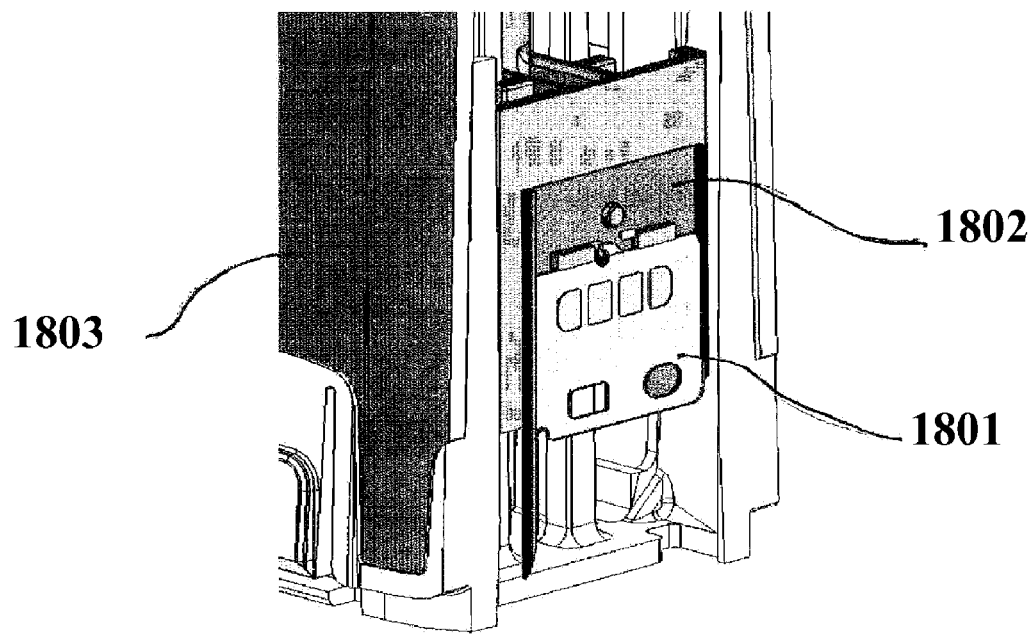
Figure 19D:
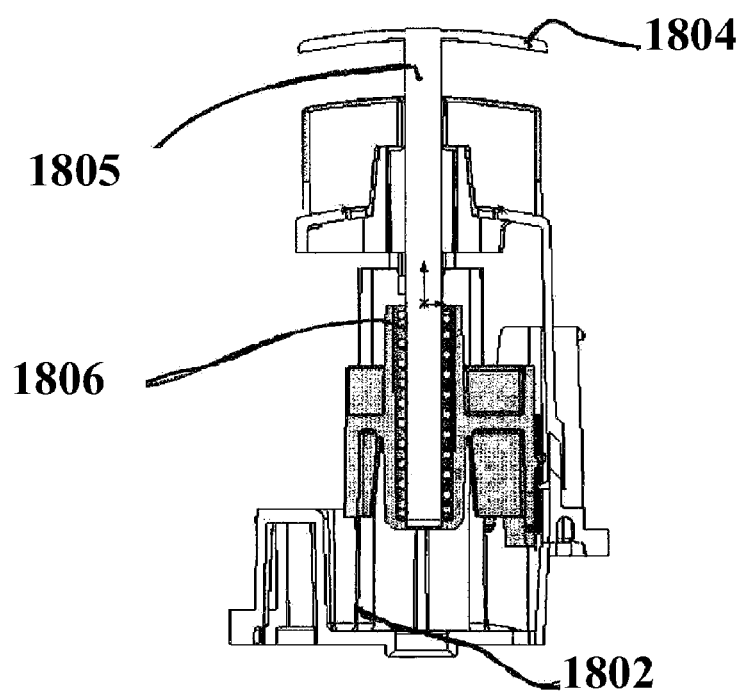

FIGS. 19B-19D illustrate a perspective view, a close-up perspective view, and a side view, respectively, of the two stage sensor insertion mechanism after the first stage trigger button firing shown in FIG. 19A, where the side view shown in FIG. 19D further illustrates the configuration of the carrier or the housing 1803 and drive spring 1806 with the plunger 1805 and the trigger button 1804.

Figure 20A:
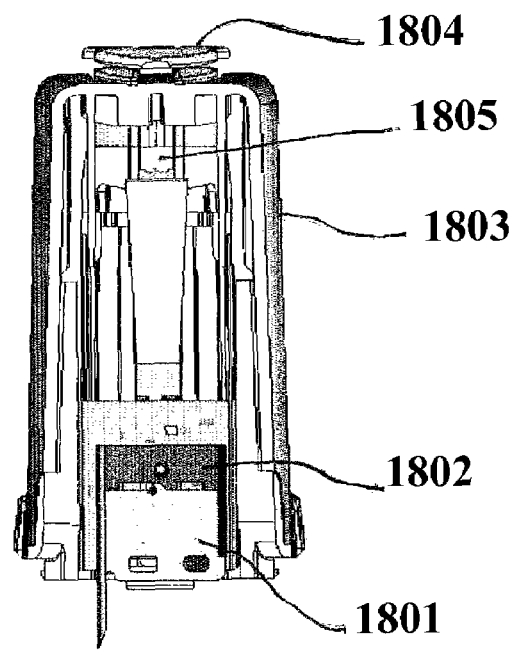
FIGS. 20A-20B illustrate the front component view and the perspective view, respectively, of the two stage sensor insertion mechanism after the sensor placement at the predetermined depth with the plunger depressed down to deliver the sensor to the maximum predetermined depth in accordance with one embodiment of the present invention.
Figure 20B:
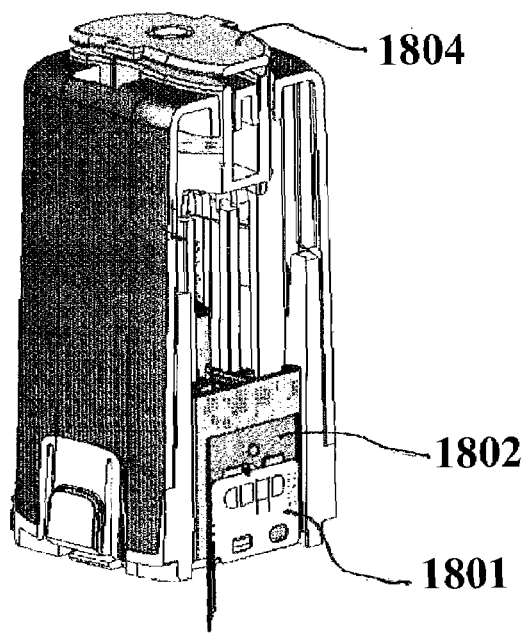

FIGS. 20A-20B illustrate the front component view and the perspective view, respectively, of the two stage sensor insertion mechanism after the sensor placement at the predetermined depth with the plunger depressed down to deliver the sensor to the maximum predetermined depth in accordance with one embodiment of the present invention.

Figure 21:
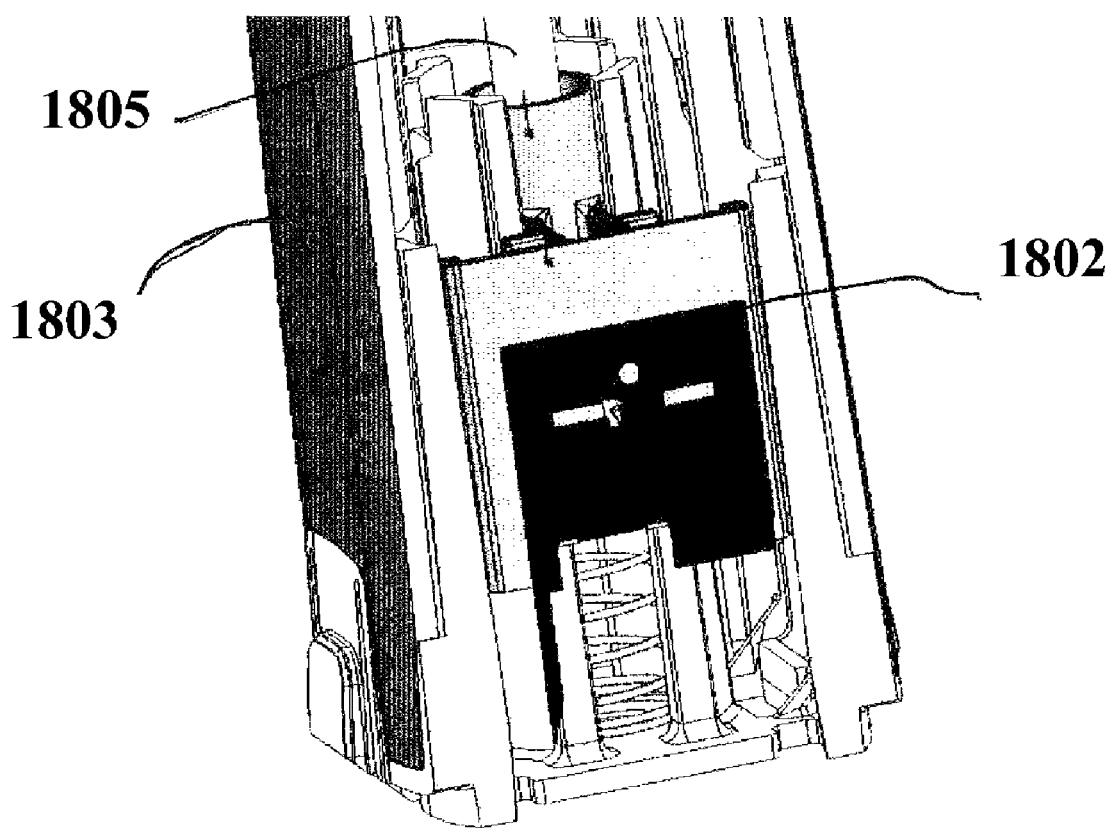
FIG. 21 illustrates a front perspective component view of the return spring of the two stage sensor insertion mechanism to retain the sensor introducer in a safe position after sensor insertion in accordance with one embodiment of the present invention, where the return spring may be configured to help retract or remove the introducer from the puncture site after sensor deployment to the predetermined depth.

FIG. 21 illustrates a front perspective component view of the return spring of the two stage sensor insertion mechanism to retain the sensor introducer in a safe position after sensor insertion in accordance with one embodiment of the present invention, where the return spring may be configured to help retract or remove the introducer from the puncture site after sensor deployment to the predetermined depth. In one embodiment, the return spring and the drive spring 1806 may be integrally formed and disposed in the housing 1803. Alternatively, in other embodiments, the return spring and the drive spring 1806 may be separate components disposed substantially within the housing 1803 of the insertion mechanism.

Figure 22A:
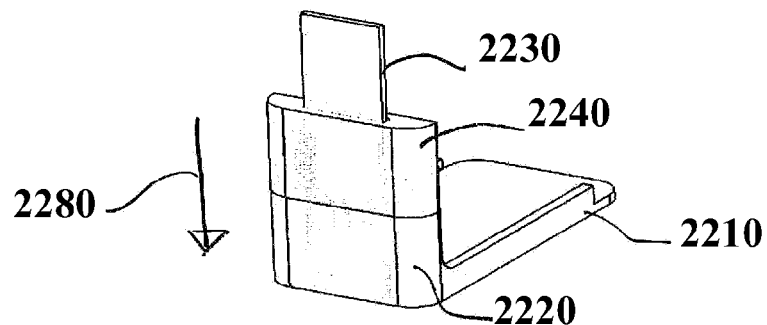
FIG. 22A is a perspective view of a first stage sensor introducer mechanism in accordance with one embodiment of the present invention.

FIG. 22A is a perspective view of a first stage sensor introducer mechanism in accordance with one embodiment of the present invention. Referring to FIG. 22A the first stage sensor introducer mechanism in one embodiment includes a mounting unit comprising a base portion 2210 and a sensor guide portion 2220. As shown, the guide portion 2220 of the mounting unit may be coupled to a sensor introducer assembly housing 2240 configured to operatively couple to a sensor introducer deployment section 2230. In one embodiment, the sensor introducer deployment section 2230 and the sensor introducer assembly housing 2240 may be configured to be detachably removed from the sensor guide portion 2220 of the mounting unit upon actuation of the sensor introducer deployment section 2230 for transcutaneous positioning of the analyte sensor through the skin layer of the patient, for example, so as to place the sensor at the first deployment position.

Referring back to FIG. 22A, in one embodiment, a sensor introducer 2250 (FIG. 22C) is provided substantially within the sensor introducer assembly housing 2240 so as to couple to the sensor introducer deployment section 2230. As such, in one embodiment, the actuation of the sensor introducer deployment section 2230, for example, by manual depression thereupon with an application of a predetermined amount of force in a substantially downward direction as shown by directional arrow 2280. In a further embodiment, the actuation of the sensor introducer deployment section 2230 may include an automated or semi-automated mechanism which the patient or the user may deploy. In such an embodiment, the deployment of the automated or semi-automated mechanism (for example, by triggering a switch) is configured to translate the sensor introducer deployment section 2230 in the downward direction so as to transcutaneously position the sensor introducer 2250 through the skin layer of the patient.

Figure 22B:
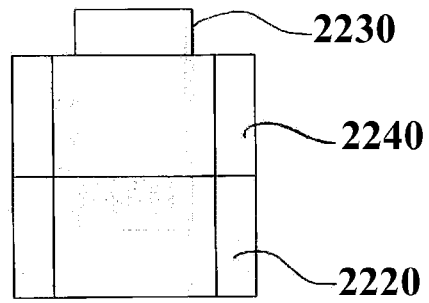
FIG. 22B is a side planar view of the first stage sensor introducer mechanism of FIG. 22A in accordance with one embodiment of the present invention.
Figure 22C:
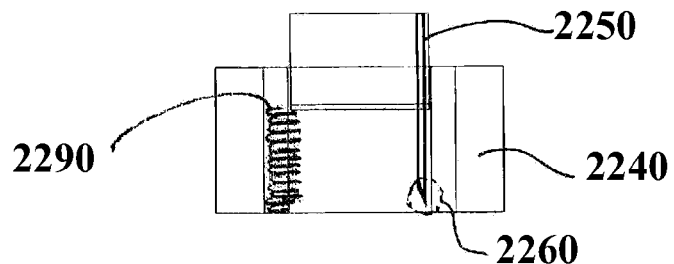
FIG. 22C is a side planar view of the sensor introducer coupled to the first stage sensor introducer mechanism of FIG. 22A in accordance with one embodiment of the present invention.

FIG. 22B is a front planar view of the first stage sensor introducer mechanism of FIG. 22A, and FIG. 22C shows the sensor introducer 2250 coupled to the sensor introducer deployment section 2240 of FIG. 22A in accordance with one embodiment of the present invention. As shown, in one embodiment, the sensor introducer 2250 is operatively coupled to the sensor introducer deployment mechanism 2230 such that the sensor introducer 2250 is moved in a downward direction upon actuation of the sensor introducer deployment mechanism 2230. Referring to FIG. 22C, in one embodiment, the sensor introducer 2250 is provided with a tip portion 2260 which is configured to coupled to a tip portion 2320 (FIG. 23A) of the sensor 2310, and further to puncture through the skin of the patient upon actuation of the sensor introducer deployment mechanism 2230 so as to position the sensor 2310 at a first predetermined subcutaneous position. Thereafter, as discussed in further detail below, the position of the sensor 2310 is further modified, for example, by the coupling of the transmitter unit 2510 (FIG. 25A) substantially on the base portion 2210 of the mounting unit.

Referring again to FIG. 22C, also shown is a return spring 2290 substantially provided in the sensor introducer assembly housing 2240, and coupled to the sensor introducer deployment mechanism 2230. In this manner, in one embodiment, the sensor introducer 2250 coupled to the sensor introducer deployment mechanism 2230 may be configured to return to its original pre-deployment position after the initial actuation or deployment of the sensor introducer deployment mechanism 2230 such that the sensor introducer 2250 is substantially removed from the sensor guide portion 2220 of the mounting unit. In this manner, upon completion of the first stage sensor positioning using the sensor introducer deployment mechanism 2230, the sensor introducer deployment mechanism 2230, the sensor introducer assembly housing 2240 and the sensor introducer 2250 may be detachably removed from the mounting unit.

Optionally, in an alternate embodiment, the sensor introducer assembly housing 2240 may be configured to be retained coupled to the sensor guide portion 2220 after the actuation of the sensor introducer deployment mechanism 2230, such that the sensor introducer assembly housing 2240 may be configured to substantially entirely house or retain the sensor introducer 2250 to avoid contact with the patient, for example. In such configuration, the sensor introducer deployment mechanism 2230 may be configured to be detachably removed from the sensor introducer assembly housing 2240 and discarded after actuation.

Figure 23A:
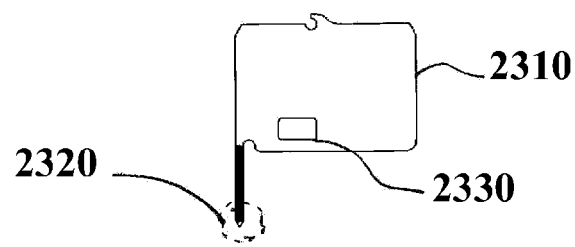
FIG. 23A is a front planar view of the sensor in accordance with one embodiment of the present invention.

FIG. 23A is a front planar view of the sensor in accordance with one embodiment of the present invention. As shown, the sensor includes a body portion 2310 and a tip portion 2320, where the tip portion 2320 in one embodiment is configured to couple to the tip portion 2260 of the sensor introducer 2250 for transcutaneous positioning. The body portion 2310 in one embodiment is provided with a plurality of contacts for establishing electrical contact with the transmitter unit. Referring again to FIG. 23A, the body portion 2310 in one embodiment may be provided with an engagement portion 2330 which is configured to mate with a portion of the transmitter unit housing.

As described in further detail below, when the transmitter unit housing 2510 is coupled to the mounting unit, in one embodiment, the transmitter unit housing 2510 may be configured to couple to the engagement portion 2330 of the sensor to displace the sensor from the first predetermined position to the second predetermined position. In this manner, in one embodiment, the sensor introducer 2250 (FIG. 22C) may be configured to transcutaneously position the sensor at the first predetermined position under the skin layer of the patient, while the transmitter unit may be configured to further displace the sensor from the first predetermined position to the second predetermined position such that the sensor tip portion 2320 is in fluid contact with the patient's analyte.

Figure 23B:
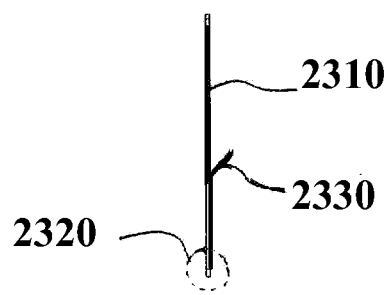
FIG. 23B is a side view of the sensor shown in FIG. 23A in accordance with one embodiment of the present invention.
Figure 23C:
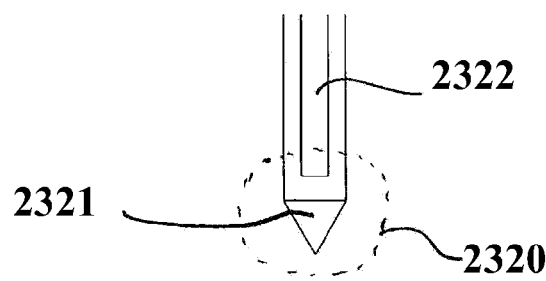
FIG. 23C is a close up view of the tip portion of the sensor shown in FIG. 23A in accordance with one embodiment of the present invention.

FIG. 23B is a side view of the sensor and FIG. 23C is a close up view of the tip portion of the sensor shown in FIG. 23A in accordance with one embodiment of the present invention. Referring to FIG. 23B, in one embodiment, the engagement portion 2330 may be configured to protrude from the sensor body portion 2310 so as to engage with the corresponding portion of the transmitter unit. Referring to FIG. 23C, the sensor tip portion 2320 in one embodiment includes a sharp tip end 2321 to facilitate the movement of the sensor from the first predetermined position to the second predetermined position substantially in response to the force applied upon the engagement portion 2330 of the sensor by the transmitter unit housing 2510. Moreover, in one embodiment, the sensor tip portion 2320 may also include a rib portion 2322 configured to provide additional rigidity to the sensor tip portion 2320 to aid the insertion process.

Figure 23D:
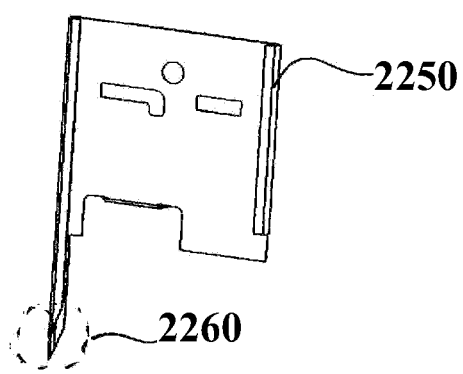
FIG. 23D is a perspective view of the sensor introducer in the first stage sensor introducer mechanism of FIG. 22A in accordance with one embodiment of the present invention.
Figure 23E:
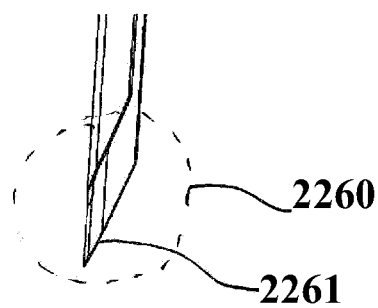
FIG. 23E is a close up view of the tip portion of the sensor introducer of FIG. 23D in accordance with one embodiment of the present invention.

FIG. 23D is a perspective view of the sensor introducer and FIG. 23E is a close up view of the tip portion of the sensor introducer in the first stage sensor introducer mechanism of FIG. 22A in accordance with one embodiment of the present invention. Referring to FIG. 23E, in one embodiment, the tip portion 2260 of the sensor introducer 2250 includes a sharp edge section 2261 configured to pierce through the skin layer of the patient when the sensor introducer deployment mechanism 2230 is actuated.

Figure 23F:
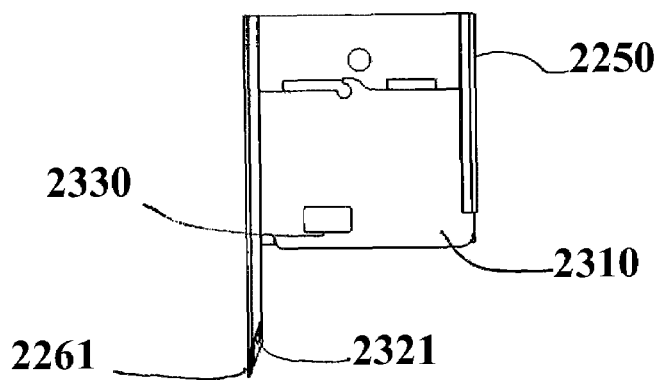
FIG. 23F is a front planar view of the sensor and sensor introducer of the first stage sensor introducer mechanism of FIG. 22A in accordance with one embodiment of the present invention.
Figure 23G:
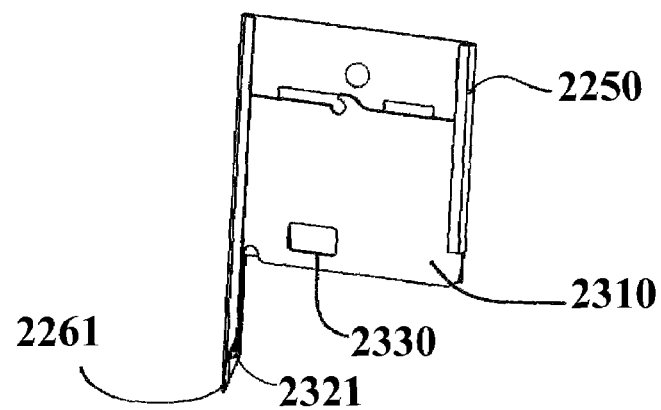
FIG. 23G is a perspective view of the sensor and sensor introducer shown in FIG. 23F in accordance with one embodiment of the present invention.
Figure 23H:
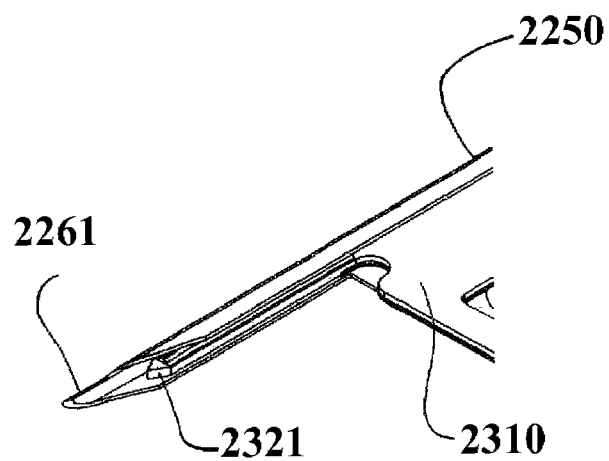
FIG. 23H is a close up view of the tip portion of the sensor and sensor introducer shown in FIG. 23F in accordance with one embodiment of the present invention.
Figure 24:
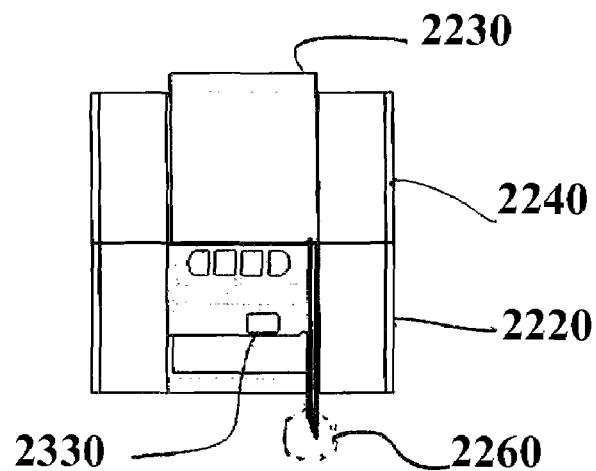
FIG. 24 is a front planar view of the first stage sensor insertion of the sensor introducer mechanism of FIG. 22A in accordance with one embodiment of the present invention.

FIG. 23F is a front planar view of the sensor and sensor introducer, FIG. 23G is a perspective view of the sensor and sensor introducer, and FIG. 23H is a close up view of the tip portion of the sensor and sensor introducer in accordance with one embodiment of the present invention. Moreover, FIG. 24 is a front planar view of the first stage sensor insertion of the sensor introducer mechanism of FIG. 22A in accordance with one embodiment of the present invention. As can be seen, in one embodiment, the tip portion 2320 of the sensor is substantially provided within the tip portion 2260 of the sensor introducer 2250 such that when the sensor introducer tip portion 2260 pierces through the skin of the patient, the tip portion 2320 of the sensor is configured to transcutaneously move with the movement of the sensor introducer 2250.

Figure 25A:
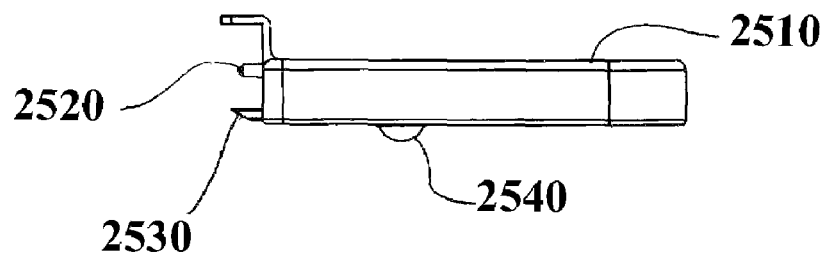
FIG. 25A is a side view of a transmitter unit for coupling to the first stage sensor introducer mechanism of FIG. 22A in accordance with one embodiment of the present invention.
Figure 25B:
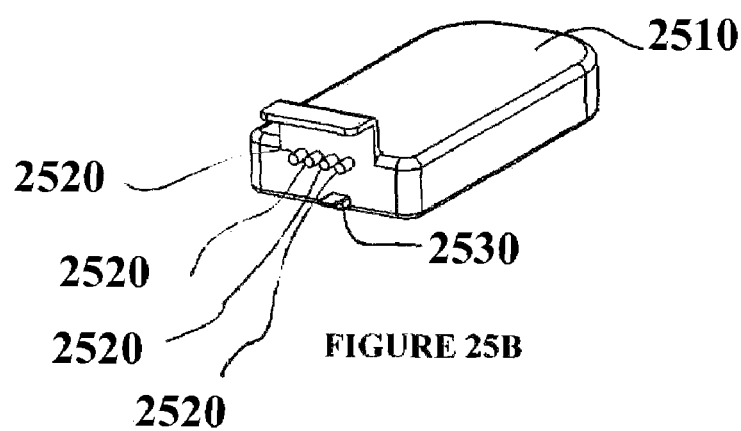
FIG. 25B is a perspective view of the transmitter unit of FIG. 25A in accordance with one embodiment of the present invention.

FIG. 25A is a side view of a transmitter unit and FIG. 25B is a perspective view of the transmitter unit of FIG. 25A in accordance with one embodiment of the present invention. Referring to FIGS. 25A-25B, in one embodiment, the transmitter unit 2510 includes a plurality of contacts 2520 each configured to establish electrical contact with a corresponding one of a plurality of contacts disposed on the sensor body 2310. Referring again to FIG. 25A, the transmitter unit 2510 in one embodiment includes a guide section 2530. In one embodiment, the guide section 2530 is configured to correspondingly couple to the engagement portion 2330 of the sensor during positioning of the transmitter unit 2510 to couple to the mounting unit. In this manner, in one embodiment, the positioning of the transmitter unit 2510 on the mounting unit provides sufficient force applied on the sensor (and in particular, at the engagement portion 2330 of the sensor) to displace the sensor from the first predetermined position to the second predetermined position.

Referring again to the Figures, a temperature detection section 2540 may in one embodiment be provided to the lower surface of the transmitter unit 2510 so as to be in physical contact with the patient's skin when the transmitter unit 2510 is coupled to the mounting unit. In this manner, the transmitter unit 2510 may be configured to monitor the on skin temperature of the patient, for example, in analyzing and processing signals received from the sensor associated with the detected analyte levels.

Figure 25C:
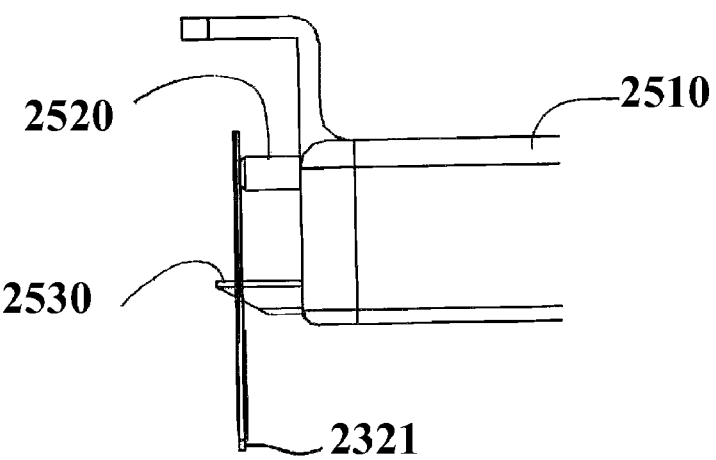
FIG. 25C is a side view of the transmitter unit engaged with the sensor for the second stage sensor insertion in accordance with one embodiment of the present invention.
Figure 25D:
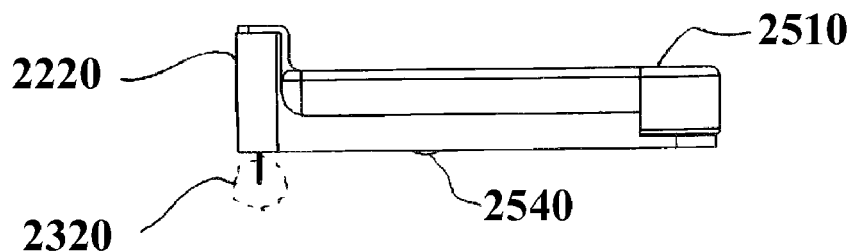
FIG. 25D is a side view of the transmitter unit mounted to the overall assembly in accordance with one embodiment of the present invention.
Figure 25E:
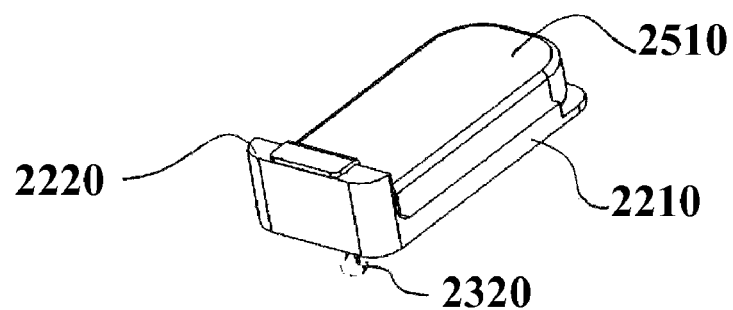
FIG. 25E is a perspective view of the transmitter unit mounted to the overall assembly of FIG. 25D in accordance with one embodiment of the present invention.

FIG. 25C is a side view of the transmitter unit engaged with the sensor for the second stage sensor insertion in accordance with one embodiment of the present invention. Furthermore, FIG. 25D is a side view of the transmitter unit and FIG. 25E is a perspective view of the transmitter unit mounted to the mounting in accordance with one embodiment of the present invention. Referring to FIG. 25C, in one embodiment, the positioning of the transmitter unit 2510 to couple to the mounting unit correspondingly engages the guide section 2530 of the transmitter unit 2510 with the engagement portion 2330 of the sensor (where the sensor is already transcutaneously positioned at the first predetermined position by the sensor introducer 2250), and with the aid of the sharp tip end 2321, positions the tip portion 2320 of the sensor at the second predetermined position in fluid contact with the patient's analyte.

Figure 26A:
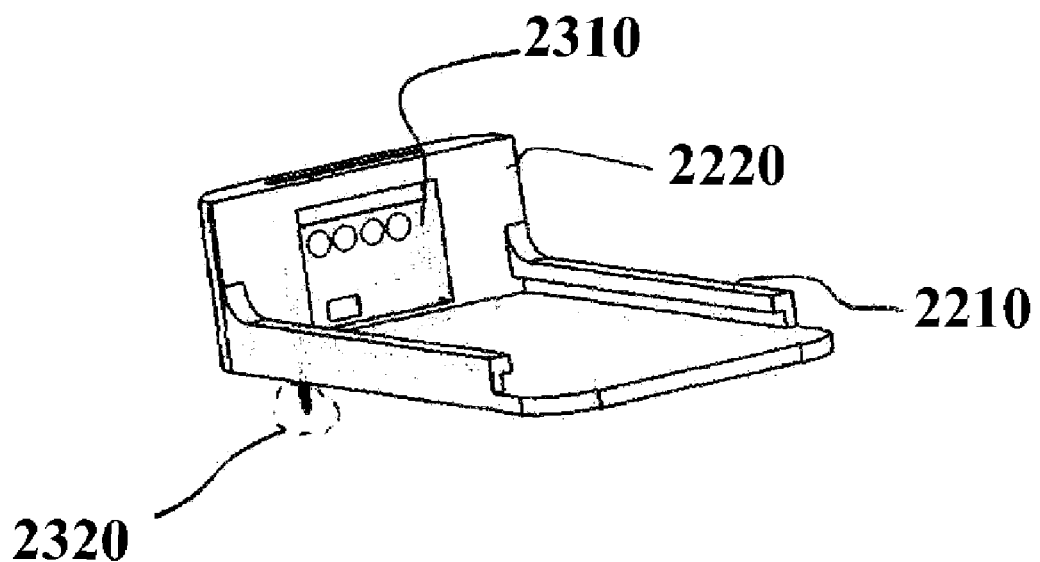
FIG. 26A is a perspective view of the sensor in the final position with respect to the sensor introducer mechanism without the transmitter unit in accordance with one embodiment of the present invention.
Figure 26B:
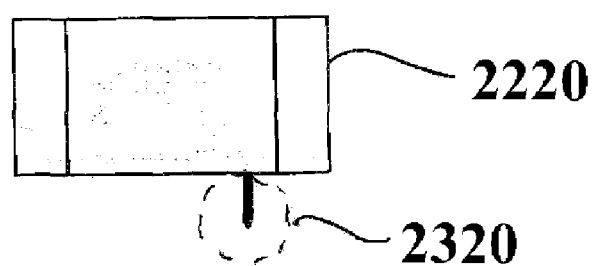
FIG. 26B is a front planar view of the sensor in the final position shown in FIG. 26A in accordance with one embodiment of the present invention.

FIG. 26A is a perspective view of the sensor in the final position (second predetermined position) with respect to the sensor introducer mechanism without the transmitter unit, and FIG. 26B is a front planar view of the sensor in the final position shown in FIG. 26A in accordance with one embodiment of the present invention.

In the manner described above, in particular embodiments, the analyte sensor deployment includes a two stage insertion process where the first transcutaneous placement is achieved by the sensor introducer 2250 at a substantially high velocity, and thereafter, a second subsequent positioning of the sensor is obtained using the manual force applied upon the transmitter unit 2510 when the transmitter unit 2510 is coupled to the mounting unit. In this manner, in one embodiment, actual or perceived pain or trauma associated with the initial skin puncture to trancutaneously position the sensor through the skin layer of the patient is substantially minimized using a high speed introduction mechanism, while the subsequent final positioning of the sensor is thereafter achieved at a relatively slower speed (for example, using manual force applied upon the transmitter unit 2510).

Figure 9:
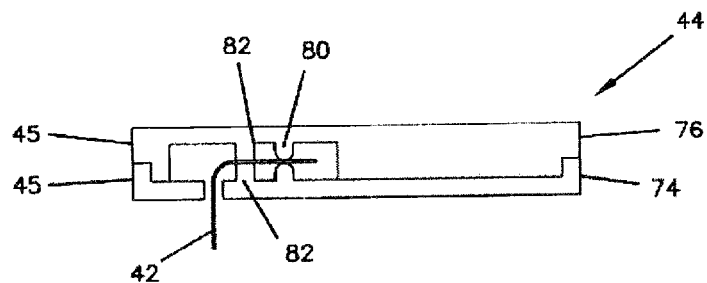
FIG. 9 is a cross-sectional view of an embodiment of an on-skin sensor control unit, according to the invention.
Figure 10:
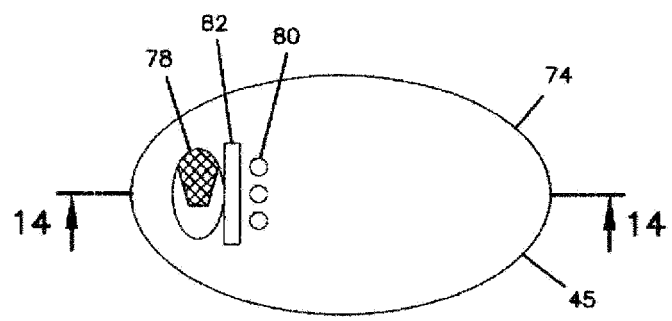
FIG. 10 is a top view of a base of an on-skin sensor control unit.
Figure 11:
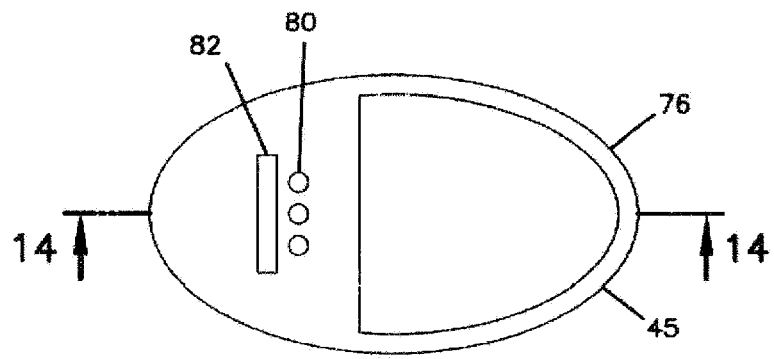
FIG. 11 is a bottom view of a cover of an on-skin sensor control unit.
Figure 12:
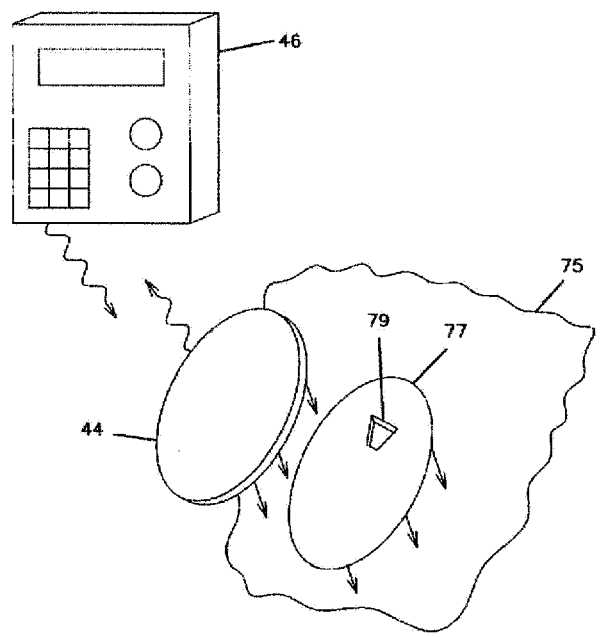
FIG. 12 is a perspective view of an on-skin sensor control unit on the skin of a patient.

Referring back to FIG. 1, the on-skin sensor control unit 44 is configured to be placed on the skin of a patient. One embodiment of the on-skin sensor control unit 44 has a thin, oval shape to enhance concealment, as illustrated in FIGS. 9-11. However, other shapes and sizes may be used. The on-skin sensor control unit 44 includes a housing 45, as illustrated in FIGS. 9-11. The on-skin sensor control unit 44 is typically attachable to the skin 75 of the patient, as illustrated in FIG. 12. Another method of attaching the housing 45 of the on-skin sensor control unit 44 to the skin 75 includes using a mounting unit 77.

The sensor 42 and the electronic components within the on-skin sensor control unit 44 are coupled via conductive contacts 80. The one or more working electrodes 58, counter electrode 60 (or counter/reference electrode), optional reference electrode 62, and optional temperature probe 66 are attached to individual conductive contacts 80. In the illustrated embodiment of FIGS. 9-11, the conductive contacts 80 are provided on the interior of the on-skin sensor control unit 44.

Figure 13A:
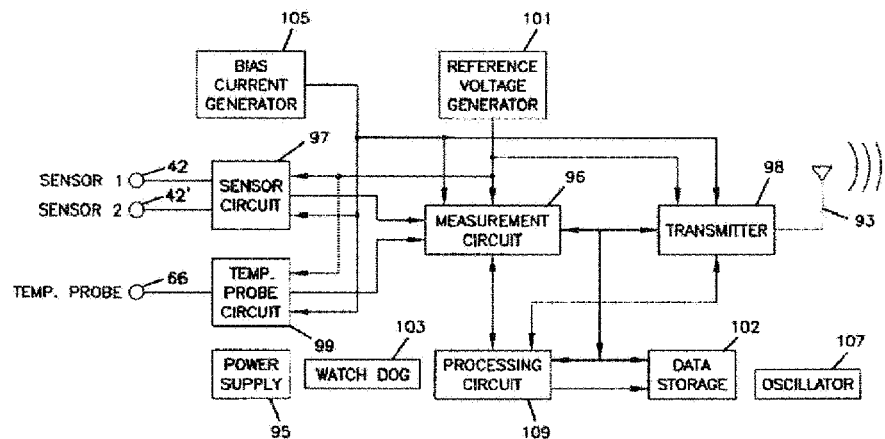
FIG. 13A is a block diagram of one embodiment of an on-skin sensor control unit, according to the invention.

Referring back to the Figures, the on-skin sensor control unit 44 may include at least a portion of the electronic components that operate the sensor 42 and the analyte monitoring device system 40. One embodiment of the electronics in the on-skin control unit 44 is illustrated as a block diagram in FIG. 13A. The electronic components of the on-skin sensor control unit 44 may include a power supply 95 for operating the on-skin control unit 44 and the sensor 42, a sensor circuit 97 for obtaining signals from and operating the sensor 42, a measurement circuit 96 that converts sensor signals to a desired format, and a processing circuit 109 that, at minimum, obtains signals from the sensor circuit 97 and/or measurement circuit 96 and provides the signals to an optional transmitter 98. In some embodiments, the processing circuit 109 may also partially or completely evaluate the signals from the sensor 42 and convey the resulting data to the optional transmitter 98 and/or activate an optional alarm system 94 (see FIG. 13B) if the analyte level exceeds a threshold. The processing circuit 109 often includes digital logic circuitry.

The on-skin sensor control unit 44 may optionally contain a transmitter or transceiver 98 for transmitting the sensor signals or processed data from the processing circuit 109 to a receiver (or transceiver)/display unit 46, 48; a data storage unit 102 for temporarily or permanently storing data from the processing circuit 109; a temperature probe circuit 99 for receiving signals from and operating a temperature probe 66; a reference voltage generator 101 for providing a reference voltage for comparison with sensor-generated signals; and/or a watchdog circuit 103 that monitors the operation of the electronic components in the on-skin sensor control unit 44.

Moreover, the sensor control unit 44 may include a bias control generator 105 to correctly bias analog and digital semiconductor devices, an oscillator 107 to provide a clock signal, and a digital logic and timing component 109 to provide timing signals and logic operations for the digital components of the circuit.

Figure 13B:
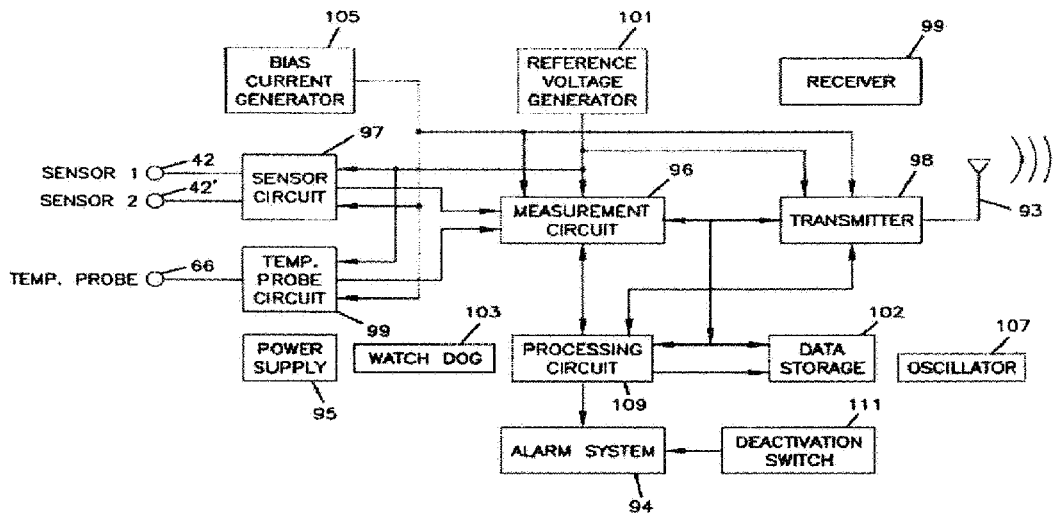
FIG. 13B is a block diagram of another embodiment of an on-skin sensor control unit, according to the invention.

FIG. 13B illustrates a block diagram of another exemplary on-skin control unit 44 that also includes optional components such as a receiver (or transceiver) 99 to receive, for example, calibration data; a calibration storage unit 100 to hold, for example, factory-set calibration data, calibration data obtained via the receiver 99 and/or operational signals received, for example, from a receiver/display unit 46, 48 or other external device; an alarm system 104 for warning the patient; and a deactivation switch 111 to turn off the alarm system.

The electronics in the on-skin sensor control unit 44 and the sensor 42 are operated using a power supply 95. The sensor control unit 44 may also optionally include a temperature probe circuit 99.

The output from the sensor circuit 97 and optional temperature probe circuit is coupled into a measurement circuit 96 that obtains signals from the sensor circuit 97 and optional temperature probe circuit 99 and, at least in some embodiments, provides output data in a form that, for example can be read by digital circuits.

In some embodiments, the data from the processing circuit 109 is analyzed and directed to an alarm system 94 (see FIG. 13B) to warn the user.

In some embodiments, the data (e.g., a current signal, a converted voltage or frequency signal, or fully or partially analyzed data) from processing circuit 109 is transmitted to one or more receiver/display units 46, 48 using a transmitter 98 in the on-skin sensor control unit 44. The transmitter has an antenna 93, such as a wire or similar conductor, formed in the housing 45.

In addition to a transmitter 98, an optional receiver 99 may be included in the on-skin sensor control unit 44. In some cases, the transmitter 98 is a transceiver, operating as both a transmitter and a receiver. The receiver 99 (and/or receiver display/units 46, 48) may be used to receive calibration data for the sensor 42. The calibration data may be used by the processing circuit 109 to correct signals from the sensor 42. This calibration data may be transmitted by the receiver/display unit 46, 48 or from some other source such as a control unit in a doctor's office.

Calibration data may be obtained in a variety of ways. For instance, the calibration data may simply be factory-determined calibration measurements which can be input into the on-skin sensor control unit 44 using the receiver 99 or may alternatively be stored in a calibration data storage unit 100 within the on-skin sensor control unit 44 itself or elsewhere such as, e.g., receiver display/units 46, 48, (in which case a receiver 99 may not be needed). The calibration data storage unit 100 may be, for example, a readable or readable/writeable memory circuit.

Alternative or additional calibration data may be provided based on tests performed by a doctor or some other professional or by the patient himself. For example, it is common for diabetic individuals to determine their own blood glucose concentration using commercially available testing kits. The result of this test is input into the on-skin sensor control unit 44 (and/or receiver display/units 46, 48) either directly, if an appropriate input device (e.g., a keypad, an optical signal receiver, or a port for connection to a keypad or computer) is incorporated in the on-skin sensor control unit 44, or indirectly by inputting the calibration data into the receiver/display unit 46, 48 and transmitting the calibration data to the on-skin sensor control unit 44.

Other methods of independently determining analyte levels may also be used to obtain calibration data. This type of calibration data may supplant or supplement factory-determined calibration values.

In some embodiments of the invention, calibration data may be required at periodic intervals, for example, about every ten hours, eight hours, about once a day, or about once a week, to confirm that accurate analyte levels are being reported. Calibration may also be required each time a new sensor 42 is implanted or if the sensor exceeds a threshold minimum or maximum value or if the rate of change in the sensor signal exceeds a threshold value. In some cases, it may be necessary to wait a period of time after the implantation of the sensor 42 before calibrating to allow the sensor 42 to achieve equilibrium. In some embodiments, the sensor 42 is calibrated only after it has been inserted. In other embodiments, no calibration of the sensor 42 is needed (e.g., a factory calibration may be sufficient).

Regardless of the type of analyte monitoring system employed, it has been observed that transient, low readings may occur for a period of time. These anomalous low readings may occur during the first hours of use, or anytime thereafter. In certain embodiments, spurious low readings may occur during the night and may be referred to as "night time dropouts". For example, in the context of an operably positioned continuous monitoring analyte sensor under the skin of a user, such spurious low readings may occur for a period of time following sensor positioning and/or during the first night post-positioning. In many instances, the low readings resolve after a period of time. However, these transient, low readings put constraints on analyte monitoring during the low reading period. Attempts to address this problem vary and include delaying calibration and/or reporting readings to the user until after this period of low readings passes after positioning of the sensor or frequent calibration of the sensor—both of which are inconvenient and neither of which is desirable.

However, as noted above embodiments of the subject invention have at least a minimal period, if at all, of spurious low readings, i.e., a substantially reduced sensor equilibration period, including substantially no equilibration period. In this regard, in those embodiments in which an initial post-positioning calibration is required, such may be performed substantially immediately after sensor positioning. For example, in certain embodiments a calibration protocol may include a first post-positioning calibration at less than about 10 hours after a sensor has been operably positioned, e.g., less than about 5 hours, e.g., less than about 3 hours, e.g., less than about 1 hour, e.g., less than about 0.5 hours. One or more additional calibrations may not be required, or may be performed at suitable times thereafter.

The on-skin sensor control unit 44 may include an optional data storage unit 102 which may be used to hold data (e.g., measurements from the sensor or processed data).

In some embodiments of the invention, the analyte monitoring device 40 includes only an on-skin control unit 44 and a sensor 42.

One or more receiver/display units 46, 48 may be provided with the analyte monitoring device 40 for easy access to the data generated by the sensor 42 and may, in some embodiments, process the signals from the on-skin sensor control unit 44 to determine the concentration or level of analyte in the subcutaneous tissue. The receiver may be a transceiver. Receivers may be palm-sized and/or may be adapted to fit on a belt or within a bag or purse that the patient carries.

Figure 14:
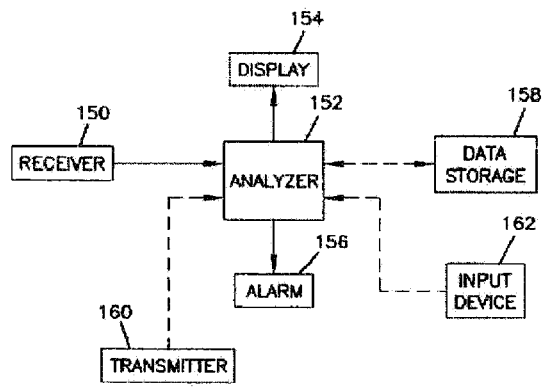
FIG. 14 is a block diagram of one embodiment of a receiver/display unit, according to the invention.

The receiver/display units 46, 48, as illustrated in block form at FIG. 14, typically include a receiver 150 to receive data from the on-skin sensor control unit 44, an analyzer 152 to evaluate the data, a display 154 to provide information to the patient, and an alarm system 156 to warn the patient when a condition arises. The receiver/display units 46, 48 may also optionally include a data storage device 158, a transmitter 160, and/or an input device 162.

Data received by the receiver 150 is then sent to an analyzer 152.

The output from the analyzer 152 is typically provided to a display 154. The receiver/display units 46, 48 may also include a number of optional items such as a data storage unit 158 store data, a transmitter 160 which can be used to transmit data, and an input device 162, such as a keypad or keyboard.

In certain embodiments, the receiver/display unit 46, 48 is integrated with a calibration unit (not shown). For example, the receiver/display unit 46, 48 may, for example, include a conventional blood glucose monitor. Devices may be used including those that operate using, for example, electrochemical and colorimetric blood glucose assays, assays of interstitial or dermal fluid, and/or non-invasive optical assays. When a calibration of the implanted sensor is needed, the patient uses the integrated in vitro monitor to generate a reading. The reading may then, for example, automatically be sent by the transmitter 160 of the receiver/display unit 46, 48 to calibrate the sensor 42.

In certain embodiments, analyte data (processed or not) may be forwarded (such as by communication) to a remote location such as a doctor's office if desired, and received there for further use (such as further processing).

Integration With a Drug Administration System

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a sensor positioning device, an on-skin sensor control unit, a receiver/display unit, a data storage and controller module, and a drug administration system. In some cases, the receiver/display unit, data storage and controller module, and drug administration system may be integrated in a single unit. The sensor-based drug delivery system may use data from the one or more sensors to provide necessary input for a control algorithm/mechanism in the data storage and controller module to adjust the administration of drugs. As an example, a glucose sensor could be used to control and adjust the administration of insulin. According to certain embodiments of the subject invention, accurate data form the one or more sensors may be obtained substantially immediately after sensor positioning to provide necessary input for a control algorithm/mechanism in the data storage and controller module to adjust the administration of drugs substantially immediately.

Kits

Finally, kits for use in practicing the subject invention are also provided. The subject kits may include one or more sensors as described herein. Embodiments may also include a sensor and/or a sensor positioning device and/or transmitter and/or receiver and/or anesthetic agent, which may or may not be independent of the sensor and/or sensor positioning device.

In addition to one or more of the above-described components, the subject kits may also include written instructions for using a sensor, e.g., positioning a sensor using a sensor positioning device and/or using a sensor to obtain analyte information. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the one or more sensors and additional reagents (e.g., control solutions), if present, until use.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An assembly, comprising:
a sensor;
a mounting unit for placement on the skin of a patient;
a sensor introducer coupled to the sensor and to the mounting unit, the sensor introducer configured to transcutaneously introduce a portion of the sensor through a skin of the patient to a first position relative to the mounting unit;
a data processing unit configured to couple to the mounting unit, the data processing unit displacing the sensor to a second position relative to the mounting unit upon coupling to the mounting unit.

2. The assembly of claim 1 wherein the first position is closer to the mounting unit of the patient than the second position.

3. The assembly of claim 1 wherein the sensor includes an engagement portion configured to couple to a housing of the data processing unit, such that the portion of the sensor is displaced with the movement of the data processing unit when coupling to the mounting unit.

4. The assembly of claim 1 wherein the data processing unit is configured to be in electrical contact with the sensor to receive one or more signals associated with an analyte of the patient.

5. The assembly of claim 4 wherein the data processing unit is coupled to the mounting unit when in electrical contact with the sensor.

6. The assembly of claim 4 wherein the data processing unit transmits data associated with the one or more signals associated with the analyte.

7. The assembly of claim 6 wherein the data processing unit wirelessly transmits the data to a remote location.

8. The assembly of claim 7 wherein the transmitted data are output at the remote location.

9. The assembly of claim 1 wherein the sensor includes a glucose sensor.

10. The assembly of claim 1 wherein the sensor introducer includes a deployment mechanism to transcutaneously introduce the portion of the sensor.

11. The assembly of claim 10 wherein the deployment mechanism is actuated to transcutaneously introduce the portion of the sensor.

12. The assembly of claim 10 wherein the deployment mechanism includes a manual deployment mechanism.

13. The assembly of claim 10 wherein the deployment mechanism includes a spring biased deployment mechanism.

14. The assembly of claim 1 wherein the sensor is positioned at the first position prior to being positioned at the second position.

15. The assembly of claim 1 wherein the sensor is maintained at the second position during the sensing time period.

16. The assembly of claim 15 wherein the sensing time period includes one of approximately three days, approximately five days, or approximately seven days.

17. The assembly of claim 1 wherein the sensor includes a working electrode formed with one or more of carbon, gold, metal alloy or a conductive polymer.

18. The assembly of claim 1 wherein the portion of the sensor is transcutaneously introduced through the skin to the first position at a first angle relative to a surface of the skin, and further, wherein the transcutaneously introduced sensor is displaced to the second position at a second angle relative to the surface of the skin.

19. The assembly of claim 18 wherein the first angle and the second angle are the same.

20. The assembly of claim 18 wherein one or more of the first angle and the second angle are approximately 90 degrees or less.

* * * * *